US008759336B2

(12) United States Patent
Hurt et al.

(10) Patent No.: US 8,759,336 B2
(45) Date of Patent: Jun. 24, 2014

(54) ANTIVIRAL COMPOUNDS

(75) Inventors: Clarence R. Hurt, Los Altos, CA (US);
Vishwanath Lingappa, San Francisco,
CA (US); Beverly Freeman, Albany, CA
(US); Andy Atuegbu, Dublin, CA (US);
Anatoliy Kitaygorodorskyy, San
Francisco, CA (US)

(73) Assignee: Prosetta Antiviral Inc., San Francisco, CA (US)

( * ) Notice: Subject to any disclaimer, the term of this patent is extended or adjusted under 35 U.S.C. 154(b) by 0 days.

(21) Appl. No.: 13/423,141

(22) Filed: Mar. 16, 2012

(65) Prior Publication Data

US 2012/0238543 A1 Sep. 20, 2012

Related U.S. Application Data

(63) Continuation-in-part of application No. 13/099,006, filed on May 2, 2011, and a continuation-in-part of application No. 13/316,423, filed on Dec. 9, 2011.

(60) Provisional application No. 61/453,571, filed on Mar. 17, 2011, provisional application No. 61/468,614, filed on Mar. 29, 2011, provisional application No. 61/477,203, filed on Apr. 20, 2011, provisional application No. 61/479,351, filed on Apr. 26, 2011, provisional application No. 61/514,825, filed on Aug. 3, 2011.

(51) Int. Cl.
*C07D 279/18* (2006.01)
*C07D 279/22* (2006.01)
*C07D 417/10* (2006.01)
*A61K 31/5415* (2006.01)

(52) U.S. Cl.
USPC .................. 514/210.2; 514/225.2; 514/224.8

(58) Field of Classification Search
USPC ........ 544/35, 37, 38; 514/210.2, 225.2, 224.8
See application file for complete search history.

(56) References Cited

U.S. PATENT DOCUMENTS

| | | | |
|---|---|---|---|
| 4,551,740 A | 11/1985 | Hung | |
| 4,604,458 A * | 8/1986 | Hung | 544/37 |
| 6,723,893 B1 | 4/2004 | Brown et al. | |
| 6,765,088 B1 | 7/2004 | Korth et al. | |
| 7,407,948 B2 | 8/2008 | Griffiths et al. | |
| 2003/0022243 A1 | 1/2003 | Kondejewski et al. | |
| 2003/0104577 A1 | 6/2003 | Lingappa | |
| 2003/0158204 A1 | 8/2003 | Galey et al. | |
| 2003/0162246 A1 | 8/2003 | Endo et al. | |
| 2006/0177813 A1 | 8/2006 | Endo | |
| 2006/0264423 A1 | 11/2006 | Wood et al. | |
| 2007/0128633 A1 | 6/2007 | Zozulya | |
| 2010/0204215 A1 | 8/2010 | Galey et al. | |

FOREIGN PATENT DOCUMENTS

| | | |
|---|---|---|
| DE | 196 40 758 | 4/1998 |
| GB | 2083488 | 3/1982 |
| KR | 10-2003-0031992 | 4/2003 |
| WO | WO 02/096896 | 12/2002 |
| WO | WO 2004/033628 | 4/2004 |
| WO | WO 2005/019828 | 3/2005 |
| WO | WO 2005/054217 | 6/2005 |
| WO | WO 2006/032847 | 3/2006 |
| WO | WO 2006/032879 | 3/2006 |
| WO | WO 2006/034219 | 3/2006 |
| WO | WO 2008/124550 | 10/2008 |

OTHER PUBLICATIONS

Robuschi, L. Sperimentale (1940), 94, 99-124.*
Amaral et al., Phenothiazines: potential management of Creutzfeldt-Jacob disease and its variants, Int. Journal of Antimicrobial Agents 18 (2001) 411-0417.
Baker-Wagner et al., "Evidence for Host Drug Targets Essential for Dengue Virus Capsid Formation", poster presented at the International Conference on Antiviral Research (ICAR) in San Francisco, CA, Apr. 25-Apr. 28, 2010.
Bewley, G.C., cDNA and deduced amino acid sequence of murine Cu-Zn superoxide dismutase, Nucleic Acids Research, vol. 16 No. 6, Mar. 25, 1988, p. 2728.
Coetzer et al., Erythrocyte Membrane Proteins in Hereditary Glucose Phosphate Isomerase Deficiency, J. Clinical Investigation 63 (4) : 552-561 (1979), abstract only.
Copeland et al., "Protein-Protein Interactions Occurring During HIV Capsid Assembly in a Cell-free Protein Synthesizing System", poster presented at the International Conference on Antiviral Research (ICAR) in San Francisco, CA, Apr. 25-Apr. 28, 2010.
Creighton T.E. Proteins, Structures and Molecular Properties, 2nd E. pp. 31-35, Aug. 1992.
Donaldson et al., Anodic oxidation of the dye materials: Methylene Blue, Acid Blue 25, Reactive Blue 2 and Reactive Blue 15 and the characterisation of novel intermediate compounds in the anodic oxidation of Methylene Blue, Journal Chemical Technology Biotechnology. 77: 756-760, 2002.
Francis et al., "Efficacy of a Small Molecule Inhibitor of Ebola Capsid Assembly in an Animal Model", poster presented at the International Conference on Antiviral Research (ICAR) in San Francisco, CA, Apr. 25-Apr. 28, 2010.
Haurum J.S., Recombinant polyclonal antibodies: the next generation of antibody therapeutics? Drug Discovery Today, 11(13/14), Jul. 2006.
Houghtaling et al., Photobiological Properties of Positively Charged Methylene Violet Analogs., Photochemistry and Photobiology, vol. 71, Issue 1, pp. 20-28, Jan. 2000.

(Continued)

*Primary Examiner* — Kahsay Habte
(74) *Attorney, Agent, or Firm* — Morgan, Lewis & Bockius LLP

(57) ABSTRACT

Novel compounds, methods, and compositions for treating various viral infections are described. In some embodiments the novel compounds of the invention are 3-oxo-phenothiazine derivatives; more specific embodiments include 3-oxo-phenothiazine derivatives having substituents at the 1-, 7-, and 9-positions of the phenothiazine parent ring. In other embodiments, the invention provides compositions and methods for treating viral infections, especially HIV.

41 Claims, No Drawings

(56) References Cited

OTHER PUBLICATIONS

Karpuj et al., "Small Molecule Therapeutics of Viruses of Families Bunyaviridae and Arenaviridae", poster presented at the International Conference on Antiviral Research (ICAR) in San Francisco, CA, Apr. 25-Apr. 28, 2010.

Lawrason et al., "Correlation between the mean corpuscular volume and reticulocytosis in phenlhydrazine anemia in swine", Blood 4 : 1256-1263 (1949).

Lingappa, Jr. et al., A Eukaryotic Cytosolic Chaperonin is Associated with a High Molecular Weight Intermediate in the Assembly of Hepatitis B Virus Capsid, a Multimeric Particle, The Journal of Cell Biology, Apr. 1994, vol. 125. No. 1. pp. 99-111.

Lingappa et al., "Overlap in Virus Specificity Leads to the Discovery of Small Molecules Active Against Rabies Virus, Monkey Pox Virus and Cytomegalovirus", poster presented at the International Conference on Antiviral Research (ICAR) in San Francisco, CA, Apr. 25-Apr. 28, 2010.

Lingappa et al., "Cell-free Protein Synthesizing Systems as Tools for Discovery of Drugs Inhibiting Viral Capsid Assembly", poster presented at the International Conference on Antiviral Research (ICAR) in San Francisco, CA, Apr. 25-Apr. 28, 2010.

Lingappa et al., "Small Molecule Inhibitors of De Novo Cell-free Capsid Assembly Effective Against Flaviridae and Togaviridae", poster presented at the International Conference on Antiviral Research (ICAR) in San Francisco, CA, Apr. 25-Apr. 28, 2010.

Long, Experimental Anemia Produced by Phenylhydrazine Derivatives, J. Clinical Investigation 11 (4): 329-339 (1926).

Lumsden et al., The Kinetics of Hematopoiesis in the Light Horse III. The Hematological Response to Hemolytic Afiernia, Can. J. Comp. Med. 39: 32-339 Jul. 1975.

Moura et al, 3,7-Bis(dialkylamino)phenothiazin-5-ium Derivatives: Biomedical Applications and Biological Activity, Current Drug Targets, 2003, vol. 4, No. 2.

Palacios et al., Panmicrobial oligonucleotide array for diagnosis of infectious diseases, Emerging Infectious Diseases, vol. 13 No. 1, p. 73-81, Jan. 2007.

Papin et al., Methylene blue photoinactivation abolishes West Nile virus infectivity in vivo, Antiviral Research, Elsevier Science BV., Amsterdam, NL vol. 68, No. 2, Nov. 1, 2005, pp. 84-87.

Pardo C A et al., Superoxide dismutase is an abundant component in cell bodies, dendrites, and axons of motor neurons and in a subset of other neurons, Proceedings of the National Academy of Sciences, vol. 92, No. 4, Feb. 14, 1995, pp. 954-958.

Pashkevich et al., Khimiya Geterotsiklicheskikh Soedinenii (1975) (3) 353-357.

Pashkevich et al., Khimiko-Farmatsevticheskii Zhurnal (1976) 10(1) 77-80.

Pashkevich et al., Khimiya Geterotsiklicheskikh Soedinenii (1978) (7) 985-990.

Petsch et al., "Discovery of Novel Small Molecule Inhibitors of Multiple Influenza-A Strains in Vivo", poster presented at the International Conference on Antiviral Research (ICAR) in San Francisco, CA, Apr. 25-Apr. 28, 2010.

Rakhit Rishi et al., An immunological epitope selective for pathological monomer-misfolded SOD1 in ALS, Nature Medicine, vol. 13, No. 6, Jun. 2007, pp. 754-759.

Rakhit Rishi et al., Monomeric Cu, Zn-superoxide dismutase is a common misfolding intermediate in the oxidation models of sporadic and familial amyotrophic lateral sclerosis, The Journal of Biological Chemistry, vol. 279, No. 15, Apr. 9, 2004, pp. 15499-15504.

Ray Soumya S. et al., Small-molecule-mediated stabilization of familial amyotrophic lateral sclerosis-linked superoxide dismutase mutants against unfolding and aggregation. Proceedings of the National Academy of Sciences, Mar. 8, 2005, vol. 102, No. 10, pp. 3639-3644.

Robuschi, L. Sperimentale (1940) 94, 99-124.

Rosenberg et al., Messenger RNA Loses the Ability to Direct in Vitro Peptide Synthesis following incubation with Cisplatin, Molecular Pharmacology 33 (6): 611-616 (1988).

Sherman L. et al., Nucleotide Sequence and Expression of Human Chromosome 21-encoded superoxide Dismutase mRNA, Proceedings of the National Academy of Sciences, Washington, DC, US, vol. 80, Sep. 1983, pp. 5465-5469.

Tai M M et al., Conformation specific antibodies directed against the Bovine Prothrombin Calcium Complex, Journal of Biological Chemistry, vol. 255, No. 7, 1980, pp. 2790-2795.

Wainwright et al., Methylene blue derivatives—suitable photoantimicrobials for blood product disinfection, International Journal of Antimicrobial Agents 16 (2000) 381-394.

Wainwright, Mark, Richard M. Giddens, Phenothiazinium photosensitisers: choices in synthesis and application, Dyes and Pigments 57 (2003) 245-257.

Wang et al., Microarray-based detection and genotyping of viral pathogens, PNAS, vol. 99, No. 24, p. 15687-15692, Nov. 26, 2002.

* cited by examiner

ANTIVIRAL COMPOUNDS

1 CROSS-REFERENCE TO RELATED APPLICATIONS

This application is a continuation-in-part of U.S. patent application Ser. No. 13/099,006 filed 2 May 2011 and is a continuation-in-part of 13/316,423 filed 9 Dec. 2011, and claims priority under 35 U.S.C. §119(e) to provisional U.S. patent application Ser. No. 61/453,571 filed 17 Mar. 2011, 61/468,614 filed 29 Mar. 2011, 61/477,203 filed 20 Apr. 2011, 61/479,351 filed 26 Apr. 2011, and 61/514,825 filed 3 Aug. 2011, the entire disclosure of U.S. patent application Ser. No. 61/453,571 filed 17 Mar. 2011 is incorporated herein by reference in its entirety and for all purposes.

2 BACKGROUND OF THE INVENTION

2.1 Field of the Invention

The present invention provides compositions and methods for preventing and treating viral infections. The present invention thus has applications in the areas of medicine, pharmacology, virology, and medicinal chemistry.

2.2 The Related Art

Few good options are available for preventing or treating viral infections. The vast majority of antiviral drugs interfere with viral replication through the inhibition of transcription of the viral genome. Commonly these drugs inhibit a specific protein involved in viral genomic transcription, such as a polymerase or transcriptase; which often produces unwanted toxicity, since viruses depend largely on host factors for viral genomic replication. Moreover, given the highly specific nature of the target, small mutations in the viral genome are often sufficient to create viral strains that are resistant to chemotherapeutics. In addition, since the drugs inhibit active viral replication, they cannot eliminate virus that is latent or sequestered in the host; thus, patients are forced to take antiviralsand endure their toxic effectsfor long periods if not indefinitely. Not surprisingly, patients on such regimens cannot continue treatment, and remain infected as well as providing a potentially continuing source of additional infections.

Thus there is a need for better antiviral chemotherapeutics and more effective strategies for identifying such chemotherapeutics. The need is especially urgent for those suffering from chronic and debilitating viral infections, such as human immunodeficiency virus (HIV) and hepatitis C(HCV), for which no good treatment exists for the reasons noted above.

But new viral threats are also on the horizon. The steady encroachment of civilization into the most remote regions of the globe has introduced the risk of exotic viral infections to the population at large. Each passing year brings an increasing number of reports of infections by hemorragic fevers, such as Ebola virus (EBOV), Marburg virus (MARB), and Rift Valley Fever virus (RVFV). Still other viral infections can cause potentially debilitating effects, such as recurrent fevers, joint pain, and fatigue; these include: Punta Toro Virus (PTV), West Nile virus (WNV), chikungunya virus (CHIKV), Easter Equine Encephalitis virus (EEEV), Wester Equine Encephalitis virus (WEEV), Lhasa virus (LASV), and Dengue virus (DENV).

By way of example, one of the additional "new" viruses (that is, new with respect to the industrialized world) is Venezuelan Equine Encephalitis virus (also called Venezuelan equine encephalomyelitis, "VEEV"). VEEV is a mosquito-borne viral disease of all equine species, including horses, asses (wild and domestic), and zebras. Equines infected with VEEV may show one or more of the following signs: fever, depression, loss of appetite weakness, and central nervous system disorders (lack of coordination, chewing movements, head pressing, "sawhorse" stance, circling, paddling motion of the limbs, and convulsions). In some cases, horses infected with VEEV may show no clinical signs before dying. The clinical signs of VEEV can be confused with those of other diseases that affect the central nervous system. These include eastern equine encephalitis, western equine encephalitis, African horse sickness, rabies, tetanus, and bacterial meningitis. VEEV might also be mistaken for toxic poisoning. Definitive diagnosis can be made by isolating the virus in a laboratory or by testing blood for the presence of antibodies to the virus.

Humans also can contract this disease. Healthy adults who become infected by the virus may experience flu-like symptoms, such as high fevers and aches; and those having weakened immune systems, as well as the young and elderly, can become more severely ill or even die.

The virus that causes VEEV is transmitted primarily by mosquitoes that bite an infected animal and then bite and feed on another animal or human. The speed with which the disease spreads depends on the subtype of the VEEV virus and the density of mosquito populations. Enzootic subtypes of VEEV are diseases endemic to certain areas. Generally these serotypes do not spread to other localities. Enzootic subtypes are associated with the rodent-mosquito transmission cycle. These forms of the virus can cause human illness but generally do not affect equine health. Epizootic subtypes, on the other hand, can spread rapidly through large populations. These forms of the virus are highly pathogenic to equines and can also affect human health. Equines, rather than rodents, are the primary animal species that carry and spread the disease. Infected equines develop an enormous quantity of virus in their circulatory system. When a blood-feeding insect feeds on such animals, it picks up this virus and transmits it to other animals or humans. Although other animals, such as cattle, swine, and dogs, can become infected, they generally do not show signs of the disease or contribute to its spread.

Naturally occurring outbreaks of VEEV are rare. In 1936, VEEV was first recognized as a disease of concern in Venezuela following a major outbreak of equine encephalomyelitis. From 1936 to 1968, equines in several South American countries suffered devastating outbreaks. In 1969, the disease moved north throughout Central America, finally reaching Mexico and Texas in 1971. The highly pathogenic form of VEEV has not occurred in the United States since 1971. However, in 1993 an outbreak of VEEV in the State of Chiapas, Mexico, prompted the U.S. Department of Agriculture to temporarily increase its surveillance activities and tighten its quarantine requirements for equine species entering the United States from Mexico. During outbreaks, the most effective way to prevent further spread of disease is to quarantine infected equines. Controlling mosquito populations through pesticide treatments and eliminating insect-breeding sites will also enhance disease control. These measures should be accompanied by a large-scale equine immunization program. Equines in the United States should be vaccinated for VEEV only when there is a serious threat that the disease could spread to this country Similar to VEEV is West Nile virus ("WNV"), which was mentioned above. West Nile virus is named for a district in Uganda where the virus was first identified in humans in 1937. Outbreaks of the virus have occurred in a number of countries throughout Europe, the Middle East, Africa, Central Asia, and Australia, since that time. WNV was first detected in the Western Hemisphere in 1999, and since then the disease has spread across North America, Mexico, Puerto Rico, the Dominican Republic, Jamaica, Guadeloupe, and El Salvador. Symptoms range from a mild, flu-like illness (fever, headache, muscle and joint pain) and a red, bumpy rash, to meningitis. In rare cases those infected will develop encephalitis, which can include high fever, a stiff neck, disorientation, paralysis, convulsions, coma, and death in about 10 percent of cases.

No cure or treatment is available for either VEEV or WNV, or the other viruses listed above; so public health experts emphasize prevention by avoiding areas where the disease has been detected or where disease vectors (usually mosquitos) have been identified. However, that approach is becoming less reasonable as the world population grows. Moreover, some officials fear that one or both of these diseases, or other similar viruses in the toga- and flaviviridae, could be "weaponized" by a hostile government or terrorist organization to immobilize military personnel or important segments of the population in an attack.

To make matters still more complicated, the above-mentioned viral threats span almost all of the recognized viral families, including the bunyaviruses, flaviviruses, filoviruses, arenaviruses, and togaviruses. Since viral families are defined in significant part by their differences in mechanism for genomic replication, therapeutic strategies that are focused on inhibiting genomic replication will be inadequate for large outbreaks of new, and especially weaponized, viruses.

Thus, there is an acute need to provide medicinal treatments for these and other viral diseases. The present invention meets these and other needs.

3 SUMMARY OF EMBODIMENTS OF THE INVENTION

In one aspect, the present invention provides novel compounds effective to treat viral diseases. In another the present invention provides methods for treating viral diseases. In a first aspect, the present invention provides compounds having the structure:

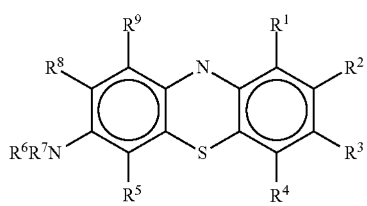

and theirpharmaceutically acceptable salts, hydrates, and coordination compounds. $R^1$, $R^2$, $R^4$, $R^5$, $R^8$, and $R^9$ are selected independently from the group consisting of: hydrogen, halo, cyano, nitro, thio, amino, carboxyl, formyl, sulfo, sulfinyl, sulfeno, sulfenamoyl, sulfonamino, and optionally substituted loweralkyl, loweralkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, loweralkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, loweralkylamino carbonyl, arylamino carbonyl, aralkylamino carbonyl, heteroarylaminocarbonyl, heteroaralkylaminocarbonyl, loweralkylcarbonylamino, arylcarbonylamino, heteroarylcarbonylamino, cycloalkyl carbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, diloweralkylamino, arylamino, diarylamino, aralkylamino, diaralkylamino, heteroarylamino, diheteroarylamino, heteroaralkylamino, diheteroaralkylamino, loweralkylsulfonyl, arylsulfonyl, heteroarylsulfonyl, cycloalkylsulfonyl, loweralkylsulfonyldioxy, arylsulfonyldioxy, heteroarylsulfonyldioxy, loweralkylsulfo, arylsulfo, heteroarylsulfo, cycloalkylsulfo, loweralkylsulfinyl, arylsulfinyl, heteroarylsulfinyl, cycloalkylsulfinyl, loweralkylsulfeno, arylsulfeno, heteroarylsulfeno, cycloalkylsulfeno, loweralkylsulfoamino, arylsulfoamino, heteroarylsulfoamino, cycloalkylsulfoamino, sulfonaloweralkylcarbonylsulfenamoyl, arylcarbonylsulfenamoyl, heteroarylcarbonylsulfenamoyl, cycloalkyl carbonylsulfenamoyl, cycloheteroalkylcarbonylsulfenamoyl, aralkylcarbonylsulfenamoyl, heteroaralkylcarbonylsulfenamoyl, (cyclo alkyl)alkylcarbonylsulfenamoyl, (cycloheteroalkyl)alkylcarbonylsulfenamoyl, diloweralkylsulfenamoyl, arylsulfenamoyl, diarylsulfenamoyl, aralkylsulfenamoyl, diaralkylsulfenamoyl, heteroarylsulfenamoyl, diheteroarylsulfenamoyl, heteroaralkylsulfenamoyl, diheteroaralkylsulfenamoyl, loweralkylcarbonylsulfinamoyl, arylcarbonylsulfinamoyl, heteroarylcarbonylsulfinamoyl, cycloalkyl carbonylsulfinamoyl, cycloheteroalkylcarbonylsulfinamoyl, aralkylcarbonylsulfinamoyl, heteroaralkylcarbonylsulfinamoyl, (cyclo alkyl)alkylcarbonylsulfinamoyl, (cycloheteroalkyl)alkylcarbonylsulfinamoyl, diloweralkylsulfinamoyl, arylsulfinamoyl diarylsulfinamoyl, aralkylsulfinamoyl, diaralkylsulfinamoyl, heteroarylsulfinamoyl, diheteroarylsulfinamoyl, heteroaralkylsulfinamoyl, diheteroaralkylsulfinamoyl, aralkycarbonylthioooxy, carbonylthio, heteroaralkylcarbonylthio, (cycloalkylloxy)carbonylthio, (cycloheteroalkyl)alkylcarbonylthio, loweralkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cyclo alkyl)alkyloxycarbonyl, (cycloheteroalkyl)alkyloxycarbonyl, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl; $R^3$ is selected from the group consisting of: halo, oxo, thio, imino, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl; and $R^6$ and $R^7$ are selected independently from the group consisting of: hydrogen and optionally substitued loweralkyl, loweralkyloxyloweralkyl, aminoloweralkyl, loweralkylaminoloweralkyl, diloweralkylaminoloweralkyl, loweralkylthioloweralkyl, aryl, aralkyl, heteroaryl, heteroaralkyl, arylcarbonyl, alkylcarbonyl, aralkylcarbonyl, heteroarylcarbonyl, and heteroaralkylcarbonyl; in addition, $R^6$ and $R^7$, together with the nitrogen atom to which each is attached, can form an optionally substitued 4-, 5-, 6-, or 7-membered ring that can include one or more ring heteroatoms, e.g., an optionally substitued cycloalkylamino or cycloheteroalkylamino ring, such as, but not limited to, optionally substituted pyrrolidinyl, piperidyl, morpholinyl, piperazinyl, azetidinyl, quinuclidinyl, and azepanyl.

In more particular embodiments, $R^3$ is oxo. In still more particular embodiments, $R^6$ and $R^7$ forms an optionally substitued pyrrolidinyl ring with the nitrogen atom to which they are attached; among these embodiments, still more particular embodiments are those in which $R^6$ and $R^7$, together with the nitrogen atom to which they are attached, is optionally substituted pyrrolidin-1-yl. Still more particular embodiments are those in which, in addition to the foregoing, at least one of $R^1$ and $R^9$ is selected form the group consisting of: halo, optionally substituted loweralkyloxy, and optionally substituted loweralkyl. Among these compounds, still more particular embodiments are those for which at least one of $R^1$ and $R^9$ is halo, and yet more particularly, those compounds wherein both $R^1$ and $R^9$ are halo, and still more particularly, those wherein $R^1$ and $R^9$ are selected from the group consisting of: chloro and fluoro. Still more particular compounds are those in which $R^3$ is oxo, $R^6$ and $R^7$, together form optionally substituted pyrrolidin-1-yl, and $R^1$ and $R^9$ are selected from the group consisting of: chloro and fluoro, especially those for which $R^1$ and $R^9$ are both chloro or both fluoro.

Among other embodiments, $R^3$ is oxo, $R^6$ and $R^7$, together form optionally substituted pyrrolidin-1-yl, and at least one of $R^1$ and $R^9$ is loweralkyloxy. In more specific embodiments, both $R^1$ and $R^9$ are methoxy.

Still other embodiments include compounds illustrated above for which $R_3$ is oxo, and $R^6$ and $R^7$, together with the nitrogen atom to which they are attached, form optionally substituted piperazinyl. Still more specific embodiments, are those in which $R^6$ and $R^7$, together with the nitrogen atom to which they are attached, form optionally substituted piperazin-1-yl. Among these compounds are still more speific embodiments in which both $R^1$ and $R^9$ are selected from the group consisting of halo and optionally substituted loweralkyl; still more specifically those in which at least one of $R^1$ and $R^9$ is halo; and yet more specifically those in which $R^1$ and $R^9$ are both chloro or both fluoro.

Still other embodiments include compounds illustrated above for which $R_3$ is oxo, and $R^6$ and $R^7$, together with the nitrogen atom to which they are attached, form optionally substituted piperazin-1-yl, and further at least one of $R^1$ and $R^9$ is loweralkyl. Yet more specific embodiments among these compounds are those compounds wherein at least one of $R^1$ and $R^9$ is methyl.

In another aspect, the present invention provides compositions and methods for treating a viral disease in a mammal afflicted with such disease, comprising administering to such mammal a therapeutically effective amount of the compound of claim 1, and more particularly viruses selected from the group consisting of HCV, HIV, influenza, Ebola virus, Marburg virus, Dengue virus, Venezuelean equine encephalitis, Chikungunya virus, and West Nile virus.

These and other aspects and advantages of the present invention will become apparent from the specification herein.

4 DETAILED DESCRIPTION OF SOME EMBODIMENTS OF THE INVENTION

4.1 Definitions

The following terms are used herein as defined below unless specifically stated otherwise:

Optionally substituted refers to the replacement of hydrogen with a univalent or divalent radical. Suitable substitution groups include, for example, hydrooxyl, nitro, amino, imino, cyano, halo, thio, thioamido, amidino, oxo, oxamidino, methoxamidino, imidino, guanidino, sulfonamido, carboxyl, formyl, loweralkyl, haloloweralkyl, loweralkoxy, halolower-alkoxy, lower alkoxyalkyl, alkylcarbonyl, arylcarbonyl, aralkylcarbonyl, heteroarylcarbonyl, heteroaralkylcarbonyl, alkylthio, aminoalkyl, cyanoalkyl, and the like as defined herein. The substitution group can itself be substituted. The group substituted onto the substitution group can be, for example, carboxyl, halo; nitro, amino, cyano, hydroxyl, loweralkyl, loweralkoxy, aminocarbonyl, —SR, thioamido, —SO$_3$H, —SO$_2$R or cycloalkyl, where R is typically hydrogen, hydroxyl or loweralkyl. When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

Loweralkyl as used herein refers to branched or straight chain alkyl groups comprising one to ten carbon atoms that independently are unsubstituted or substituted, e.g., with one or more halogen, hydroxyl or other groups. Examples of loweralkyl groups include, but are not limited to, methyl, ethyl, propyl, isopropyl, n-butyl, t-butyl, n-hexyl, neopentyl, trifluoromethyl, pentafluoroethyl, and the like.

Alkylenyl refers to a divalent straight chain or branched chain saturated aliphatic radical having from 1- to 20 carbon atoms. Typical alkylenyl groups employed in compounds of the present invention are loweralkylenyl groups that have from 1 to about 6 carbon atoms in their backbone.

Alkenyl refers herein to straight chain, branched, or cyclic radicals having one or more double bonds and from 2 to 20 carbon atoms.

Alkynyl refers herein to straight chain, branched, or cyclic radicals having one or more triple bonds and from 2 to 20 carbon atoms.

Haloloweralkyl refers to a loweralkyl radical substituted with one or more halogen atoms.

Loweralkoxy as used herein refers to RO— wherein R is loweralkyl. Representative examples of loweralkoxy groups include methoxy, ethoxy, t-butoxy, trifluoromethoxy and the like.

Loweralkythio as used herein refers to RS— wherein R is loweralkyl.

Alkoxyalkyl refers to the group-alk$_1$-O-alk$_2$, where alk$_1$ is alkylenyl or alkenyl, and alk$_2$ is alkyl or alkenyl.

Loweralkoxyalkyl refers to an alkoxyalkyl as defined above, where alk$_1$ is loweralkylenyl or loweralkenyl, and alk$_2$ is loweralkyl or loweralkenyl.

Aryloxyalkyl refers to the group alkylenyl—O-aryl. The term

Aralkoxyalkyl refers to the group alkylenyl—O-aralkyl, where aralkyl is a loweraralkyl.

Cycloalkyl refers to a mono- or polycyclic, loweralkyl substituent. Typical cycloalkyl substituents have from 3 to 8 backbone (i.e., ring) atoms in which each backbone atom is optionally substituted carbon. When used in context with cycloalkyl substituents, the term polycyclic refers herein to fused, non-fused cyclic carbon structures and spirocycles. Examples of cycloalkyl groups include, but are not limited to, cyclopropyl, cyclobutyl, cyclopentyl, cyclohexyl, adamantyl, bornyl, norbornyl, and the like.

Cycloheteroalkyl refers herein to cycloalkyl substituents that have from 1 to 5, and more typically from 1 to 4 heteroatoms (i.e., non-carbon atoms such as nitrogen, sulfur, and oxygen) in the ring structure, with the balance of atoms in the ring being optionally substituted carbon. Representative heterocycloalkyl moieties include, for example, morpholino, piperazinyl, piperidinyl, pyrrolidinyl, methylpryolidinyl, pyrrolidinone-yl, and the like.

(Cycloalkyl)alkyl and (Cycloheteroalkyl)alkyl refer to alkyl chains substituted with cycloalkyl and cycloheteroalkyl groups respectively.

Haloalkoxy refers to an alkoxy radical substituted with one or more halogen atoms. The term haloloweralkoxy refers to a loweralkoxy radical substituted with one or more halogen atoms.

Halo refers herein to a halogen radical, such as fluorine, chlorine, bromine, or iodine.

Aryl refers to monocyclic and polycyclic aromatic groups, or fused ring systems having at least one aromatic ring, having from 3 to 14 backbone carbon atoms. Examples of aryl groups include without limitation phenyl, naphthyl, dihydronaphtyl, tetrahydronaphthyl, and the like.

Aralkyl refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Heteroaryl refers herein to aryl groups having from one to four heteroatoms as ring atoms in an aromatic ring with the remainder of the ring atoms being aromatic or non-aromatic carbon atoms. When used in connection with aryl substituents, the term polycyclic refers herein to fused and non-fused cyclic structures in which at least one cyclic structure is aromatic, such as, for example, benzodioxozolo, naphthyl, and the like. Exemplary heteroaryl moieties employed as substituents in compounds of the present invention include pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

Amino refers herein to the group —$NH_2$. The term loweralkylamino refers herein to the group —NRR' where R and R' are each independently selected from hydrogen or loweralkyl. The term arylamino refers herein to the group —NRR' where R is aryl and R' is hydrogen, loweralkyl, aryl, or aralkyl. The term aralkylamino refers herein to the group —NRR' where R is aralkyl and R' is hydrogen, loweralkyl, aryl, or aralkyl. The terms heteroarylamino and heteroaralkylamino are defined by analogy to arylamino and aralkylamino.

Aminocarbonyl refers herein to the group —C(O)—$NH_2$. The terms loweralkylaminocarbonyl, arylaminocarbonyl, aralkylaminocarbonyl, heteroarylaminocarbonyl, and heteroaralkylaminocarbonyl refer to —C(O)NRR' where R and R' independently are hydrogen and optionally substituted loweralkyl, aryl, aralkyl, heteroaryl, and heteroaralkyl respectively by analogy to the corresponding terms above.

Thio refers to —SH. The terms loweralkylthio, arylthio, heteroarylthio, cycloalkylthio, cycloheteroalkylthio, aralkylthio, heteroaralkylthio, (cycloalkyl)alkylthio, and (cycloheteroalkyl)alkylthio refer to —SR, where R is optionally substituted loweralkyl, aryl, heteroaryl, cycloalkyl, cycloheteroalkyl, aralkyl, heteroaralkyl, (cycloalkyl) alkyl, and (cycloheteroalkyl)alkyl respectively.

Sulfonyl refers herein to the group —$SO_2$—. The terms loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, and (cycloheteroalkyl-) alkylsulfonyl refer to —$SO_2$R where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Sulfinyl refers herein to the group —SO—. The terms loweralkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, and (cycloheteroalkyl)alkylsulfinyl refer to —SOR where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Formyl refers to —C(O)H.

Carboxyl refers to —C(O)OH.

Carbonyl refers to the divalent group —C(O)—. The terms loweralkylcarbonyl, arylcarbonyl, heteroarylcarbonyl, cycloalkylcarbonyl, cycloheteroalkylcarbonyl, aralkycarbonyl, hetero aralkylcarbonyl, (cyclo alkyl)alkylcarbonyl, and (cycloheteroalkyl)alkylcarbonyl refer to —C(O)R, where R is optionally substituted loweralkyl, aryl, heteroaryl, cycloalkyl, cycloheteroalkyl, aralkyl, heteroaralkyl, (cycloalkyl) alkyl, and (cycloheteroalkyl)alkyl respectively.

Thiocarbonyl refers to the group —C(S)—. The terms loweralkylthiocarbonyl, arylthio carbonyl, heteroarylthio carbonyl, cyclo alkylthiocarbonyl, cyclohetero alkylthio carbonyl, aralkylthiocarbonyloxlthiocarbonyl, heteroaralkylthio carbonyl, (cyclo alkyl)alkylthio carbonyl, and (cycloheteroalkyl)alkylthio carbonyl refer to —C(S)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Carbonyloxy refers generally to the group —C(O)—O—. The terms loweralkylcarbonyloxy, arylcarbonyloxy, hetero arylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy refer to —C(O)OR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Oxycarbonyl refers to the group —O—C(O)—. The terms loweralkyloxycarbonyl, aryloxycarbonyl, heteroaryloxycarbonyl, cycloalkyloxycarbonyl, cycloheteroalkyloxy carbonyl, aralkyloxy carbonyloxycarbonyl, heteroaralkyloxy carbonyl, (cycloalkyl)alkyloxy carbonyl, (cyclo heteroalkyl) alkyloxy carbonyl refer to —O—C(O)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Carbonylamino refers to the group —NH—C(O)—. The terms loweralkyl carbonylamino, arylcarbonylamino, hetero arylcarbonylamino, cycloalkyl carbonylamino, cycloheteroalkylcarbonylamino, aralkylcarbonylamino, hetero aralkylcarbonylamino, (cycloalkyl)alkylcarbonylamino, and (cycloheteroalkyl)alkylcarbonylamino refer to —NH—C(O) R—, where R is optionally substituted loweralkyl, aryl, heteroaryl, cycloalkyl, cycloheteroalkyl, aralkyl, heteroaralkyl, (cycloalkyl)alkyl, or (cycloheteroalkyl)alkyl respectively. In addition, the present invention includes n-substituted carbonylamino (—NR'C(O)R), where R' is optionally substituted loweralkyl, aryl, heteroaryl, aralkyl, or heteroaralkyl and R retains the previous defintion.

Carbonylthio refers to the group —C(O)—S—. The terms loweralkylcarbonylthio, arylcarbonylthio, heteroarylcarbonylthio, cycloalkylcarbonylthio, cycloheteroalkylcarbonylthio, aralkylcarbonylthio, hetero aralkylcarbonylthio, (cycloalkyl)alkylcarbonylthio, (cycloheteroalkyl) alkylcarbonylthio refer to —C(O)SR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Guanidino or Guanidyl refers to substituents having a skeleton derived from guanidine, $H_2N$—C(=NH)—$NH_2$. Such moieties include those bonded at the nitrogen atom carrying the formal double bond (the 2-position of the guanidine, e.g., diaminomethyleneamino, $((H_2N)_2$—C=NH—) and those bonded at either of the nitrogen atoms carrying a formal single bond (the 1- or 3-positions of the guanidine, e.g., $H_2N$—C(=NH)—NH—). The hydrogen atoms at either nitrogen can be replaced with a suitable substituent, such as loweralkyl, aryl, or loweraralkyl.

Amidino refers to the moieties R—C(=N)—NR'— (the radical being at the $N^1$ nitrogen) and R(NR')C=N— (the radical being at the $N^2$-nitrogen), where R and R' can be hydrogen, loweralkyl, aryl, or loweraralkyl.

Imino refers to the group —C(=NR)—, where R can be hydrogen or optionally substituted loweralkyl, aryl, heteroaryl, or heteroaralkyl respectively. The terms iminoloweralkyl, imino cyclo alkyl, imino cycloheteroalkyl, iminoaralkyl, iminoheteroaralkyl, (cycloalkyl)iminoalkyl, (cycloiminoalkyl)alkyl, (cyclo iminoheteroalkyl)alkyl, and (cycloheteroalkyl)iminoalkyl refer to optionally substituted loweralkyl, cycloalkyl, cycloheteroalkyl, aralkyl, heteroaralkyl, (cycloalkyl)alkyl, and (cycloheteroalkyl)alkyl groups that include an imino group, respectively.

Oximino refers to the group —C(=NOR)—, where R can be hydrogen (hydroximino) or optionally substituted loweralkyl, aryl, heteroaryl, or heteroaralkyl respectively. The terms oximinoloweralkyl, oximinocycloalkyl, oximinocycloheteroalkyl, oximino aralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl refer to optionally substituted loweralkyl, cycloalkyl, cycloheteroalkyl, aralkyl, heteroaralkyl, (cycloalkyl)alkyl, and (cycloheteroalkyl)alkyl groups that include an oximino group, respectively.

Methylene as used herein refers to an unsubstituted, monosubstituted, or disubstituted carbon atom having a formal $sp^a$ hybridization (i.e., —CRR'—, where R and R' are hydrogen or independent substituents).

Methine as used herein refers to an unsubstituted or substituted carbon atom having a formal $sp^2$ hybridization (i.e., CR= or =CR—, where R is hydrogen or a substituent).

4.2 Compounds of the Invention

In a first aspect, the present invention provides novel compounds seleted from compounds having the structure (Compound 1):

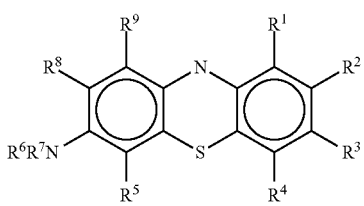

1 and their pharmaceutically acceptable salts, hydrates, and coordination compounds. $R^1$, $R^2$, $R^4$, $R^5$, $R^8$, and $R^9$ are selected independently from the group consisting of: hydrogen, halo, cyano, nitro, thio, amino, carboxyl, formyl, sulfo, sulfinyl, sulfeno, sulfenamoyl, sulfonamino, and optionally substituted loweralkyl, loweralkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, loweralkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyb heteroaralkylaminocarbonyl, loweralkylcarbonylamino, arylcarbonylamino, heteroarylcarbonylamino, cycloalkyl carbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, diloweralkylamino, arylamino, diarylamino, aralkylamino, diaralkylamino, heteroarylamino, diheteroarylamino, heteroaralkylamino, diheteroaralkylamino, loweralkylsulfonyl, arylsulfonyl, heteroarylsulfonyl, cycloalkylsulfonyl, loweralkylsulfonyldioxy, arylsulfonyldioxy, heteroarylsulfonyldioxy, loweralkylsulfo, arylsulfo, heteroarylsulfo, cycloalkylsulfo, loweralkylsulfinyl, arylsulfinyl, heteroarylsulfinyl, cycloalkylsulfinyl, loweralkylsulfeno, arylsulfeno, heteroarylsulfeno, cycloalkylsulfeno, loweralkylsulfoamino, arylsulfoamino, heteroarylsulfoamino, cycloalkylsulfoamino, sulfonaloweralkylcarbonylsulfenamoyl, arylcarbonylsulfenamoyl, heteroarylcarbonylsulfenamoyl, cycloalkyl carbonylsulfenamoyl, cycloheteroalkylcarbonylsulfenamoyl, aralkylcarbonylsulfenamoyl, heteroaralkylcarbonylsulfenamoyl, (cycloalkyl)alkylcarbonylsulfenamoyl, (cycloheteroalkyl)alkylcarbonylsulfenamoyl, diloweralkylsulfenamoyl, arylsulfenamoyl, diarylsulfenamoyl, aralkylsulfenamoyl, diaralkylsulfenamoyl, heteroarylsulfenamoyl, diheteroarylsulfenamoyl, heteroaralkylsulfenamoyl, diheteroaralkylsulfenamoyl, loweralkylcarbonylsulfinamoyl, arylcarbonylsulfinamoyl, heteroarylcarbonylsulfinamoyl, cycloalkyl carbonylsulfinamoyl, cycloheteroalkylcarbonylsulfinamoyl, aralkylcarbonylsulfinamoyl, heteroaralkylcarbonylsulfinamoyl, (cycloalkyl)alkylcarbonylsulfinamoyl, (cycloheteroalkyl)alkylcarbonylsulfinamoyl, diloweralkylsulfinamoyl, arylsulfinamoyl, diarylsulfinamoyl, aralkylsulfinamoyl, diaralkylsulfinamoyl, heteroarylsulfinamoyl, diheteroarylsulfinamoyl, heteroaralkylsulfinamoyl, diheteroaralkylsulfinamoyl, aralkycarbonylthioooxy, carbonylthio, heteroaralkylcarbonylthio, (cycloalkylloxy)carbonylthio, (cycloheteroalkyl)alkylcarbonylthio, loweralkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl. $R^3$ is selected from the group consisting of: halo, oxo, thio, imino, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl. $R^6$ and $R^7$ are selected independently from the group consisting of: hydrogen and optionally substitued loweralkyl, aryl, aralkyl, heteroaryl, heteroaralkyl, arylcarbonyl, alkylcarbonyl, aralkylcarbonyl, heteroarylcarbonyl, and heteroaralkylcarbonyl; in addition, $R^6$ and $R^7$ can form independently an optionally substitued pyrrolidyl ring with the nitrogen atom to which they are attached.

Those having ordinary skill in the art will appreciate that compounds having the structure of Compound 1 can exist in a variety of formal hybridization structures; thus, the structural formula for Compound 1 shown above implicitly includes all equivalent resonance structures. Similarly, the illustration of any specific resonance structure herein is defined to include all equivalent resonance structures implicitly unless specifically noted otherwise. The identification of such resonance structures and their equivalents is well known to persons having ordinary skill in the art.

In some embodiments $R^3$ of Compound 1 is oxo. Among these compounds, more specific embodiments include those in which $R^3$ is oxo and $R^6$ and $R^7$ are optionally substituted loweralkyl, alkyloxyalkyl, alkylaminoalkyl, and dialkylaminoalkyl; in addition, $R^6$ and $R^7$, together with the nitrogen atom to which they are attached, can form an optionally substituted cycloalkylamino or cycloheteroalkyl ring, such as, but not limited to, optionally substituted pyrollidinyl, piperidyl, morpholinyl, piperazinyl, azetidinyl, quinuclidinyl, and azepanyl. Such compounds are illustrated by the generic structure of Compound 2:

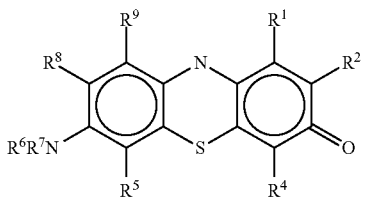

2 and their pharmaceutically acceptable salts, hydrates, and coordination compounds. The remaining substituents shown in Compound 2 are otherwise the same as those described above for Compound 1.

In still more specific embodiments for Compound 2, $R^6$ and $R^7$, together with the nitrogen atom to which they are attached, form an optionally substituted pyrrolidinyl ring; in more specific embodiments, the ring so formed is pyrrolidin-1-yl (Compound 3):

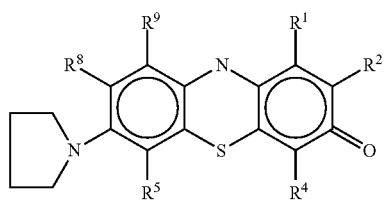

3 and their pharmaceutically acceptable salts, hydrates, and coordination compounds. The remaining substituents shown in Compound 3 are otherwise the same as those described above for Compound 1.

Included among the embodiments are compounds in which the substituents are the same as described above for Compound 3 and wherein $R^6$ and $R^7$ form an optionally substituted pyrrolidinyl ring with the nitrogen atom to which they are attached, are those in which at least one of $R^1$ and $R^9$ is selected form the group consisting of: halo, optionally substituted loweralkyoxy, and optionally substituted loweralkyl; and, more specifically, wherein at least one of $R^1$ and $R^9$ is halo. In some of these embodiments, at least one of $R^1$ and $R^9$ is halo; in other embodiments, both of $R^1$ and $R^9$ are halo. In yet more specific embodiments, $R^1$ and $R^9$ are selected from the group consisting of: chloro and fluoro, and in even more specific embodiments, $R^1$ and $R^9$ are both chloro or both fluoro. Among the latter embodiments are those in which $R^6$ and $R^7$, together with the nitrogen atom to which they are attached, is pyrrolidin-1-yl.

Included among the embodiments are compounds in which the substituents are the same as described above for Compound 3 and wherein $R^6$ and $R^7$ form an optionally substituted pyrrolidinyl ring with the nitrogen atom to which they are attached, are those in which at least one of $R^1$ and $R^9$ is optionally substituted loweralkyoxy; and, more specifically, wherein at least one of $R^1$ and $R^9$ is loweralkyloxy. In some of these embodiments, at least one of $R^1$ and $R^9$ is halo; in other embodiments, both of $R^1$ and $R^9$ are loweralkyloxy. In yet more specific embodiments, $R^1$ and $R^9$ are selected from the group consisting of: ethoxy and methoxy, and in even more specific embodiments, $R^1$ and $R^9$ are both ethoxy or both methoxy. Among the latter embodiments are those in which $R^6$ and $R^7$, together with the nitrogen atom to which they are attached, is pyrrolidin-1-yl.

In still other embodiments in which the substituents are the same as described above for Compound 3 and $R^6$ and $R^7$ form an optionally substituted pyrrolidinyl ring with the nitrogen atom to which they are attached, are compounds in which at least one of $R^1$ and $R^9$ is loweralkyl, and, more specifically, wherein at least one of $R^1$ and $R^9$ is methyl or ethyl. In yet more specific embodiments, $R^1$ and $R^9$ are both methyl or both ethyl. Among the latter embodiments are those in which $R^6$ and $R^7$, together with the nitrogen atom to which they are attached, is pyrrolidin-1-yl.

Among the specific embodiments of Compound 3 in which $R^6$ and $R^7$, together with the nitrogen atom to which they are attached, is pyrrolidin-1-yl are those in which each of $R^1$, $R^2$, $R^4$, $R^5$, $R^8$, and $R^9$ is hydrogen; each of $R^1$, $R^2$, $R^4$, $R^5$, and $R^8$ is hydrogen and $R^9$ is cyano; each of $R^2$, $R^4$, $R^5$, and $R^8$ is hydrogen, and each of $R^1$ and $R^9$ is methoxy; each of $R^2$, $R^4$, $R^5$, and $R^8$ is hydrogen, and each of $R^1$ and $R^9$ is methyl; and each of $R^2$, $R^4$, $R^5$, and $R^8$ is hydrogen, and each of $R^1$ and $R^9$ is chloro. The biological activities for these embodiments are shown in the Appendix.

In still other embodiments $R^3$ is oxo and $R^6$ and $R^7$ are optionally substituted lower alkyl or optionally substituted loweralkyloxyloweralkyl; in yet more specific embodiments $R^6$ and $R^7$ are optionally substituted methyl, ethyl, or propyl. In still more specific embodiments, $R^6$ and $R^7$ are optionally substituted methyl; and yet more specifically $R^6$ and $R^7$ are methyl, providing compounds having the generic structure of Compound 4:

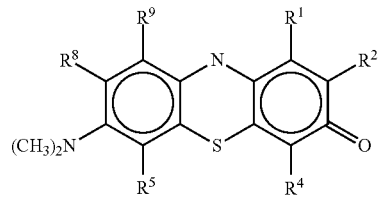

4 and their pharmaceutically acceptable salts, hydrates, and coordination compounds. The remaining substituents are the same as described above for Compound 1. In more specific embodiments, the invention provides compounds having the structure shown in Compound 4 in which each of $R^1$, $R^2$, $R^4$, $R^5$, $R^8$, and $R^9$ is hydrogen; each of $R^2$, $R^4$, $R^5$, and $R^8$ is hydrogen, and each of $R^1$ and $R^9$ is methyl; and each of $R^2$, $R^4$, $R^5$, and $R^8$ is hydrogen, and each of $R^1$ and $R^9$ is chloro.

In still more specific embodiments for Compound 2, $R^6$ and $R^7$, together with the nitrogen atom to which they are attached, form an optionally substituted piperazinyl ring; in more specific embodiments, the ring so formed is piperazin-1-yl (Compound 5):

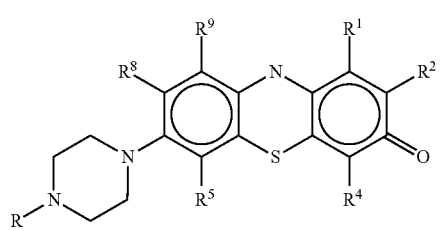

5 and their pharmaceutically acceptable salts, hydrates, and coordination compounds. The remaining substituents shown in Compound 5 are otherwise the same as those described above for Compound 1.

Included among the embodiments are compounds in which the substituents are the same as described above for Compound 5 and wherein $R^6$ and $R^7$ form an optionally substituted piperazinyl ring with the nitrogen atom to which they are attached, are those in which at least one of $R^1$ and $R^9$ is selected form the group consisting of: halo, optionally substituted loweralkyoxy, and optionally substituted loweralkyl; and, more specifically, wherein at least one of $R^1$ and $R^9$ is halo. In some of these embodiments, at least one of $R^1$ and $R^9$ is halo; in other embodiments, both of $R^1$ and $R^9$ are halo. In yet more specific embodiments, $R^1$ and $R^9$ are selected from the group consisting of: chloro and fluoro, and in even more specific embodiments, $R^1$ and $R^9$ are both chloro or both fluoro. Among the latter embodiments are those in which $R^6$ and $R^7$, together with the nitrogen atom to which they are attached, is piperazin-1-yl.

Included among the embodiments are compounds in which the substituents are the same as described above for Compound 5 and wherein $R^6$ and $R^7$ form an optionally substituted piperazinyl ring with the nitrogen atom to which they are attached, are those in which at least one of $R^1$ and $R^9$ is optionally substituted loweralkyoxy; and, more specifically, wherein at least one of $R^1$ and $R^9$ is loweralkyloxy. In some of these embodiments, at least one of $R^1$ and $R^9$ is halo; in other embodiments, both of $R^1$ and $R^9$ are loweralkyloxy. In yet more specific embodiments, $R^1$ and $R^9$ are selected from the group consisting of: ethoxy and methoxy, and in even more specific embodiments, $R^1$ and $R^9$ are both ethoxy or both methoxy. Among the latter embodiments are those in which $R^6$ and $R^7$, together with the nitrogen atom to which they are attached, is piperazin-1-yl.

In still other embodiments in which the substituents are the same as described above for Compound 5 and $R^6$ and $R^7$ form an optionally substituted piperazinyl ring with the nitrogen atom to which they are attached, are compounds in which at least one of $R^1$ and $R^9$ is loweralkyl, and, more specifically, wherein at least one of $R^1$ and $R^9$ is methyl or ethyl. In yet more specific embodiments, $R^1$ and $R^9$ are both methyl or both ethyl. Among the latter embodiments are those in which $R^6$ and $R^7$, together with the nitrogen atom to which they are attached, is piperazin-1-yl.

Among the specific embodiments of Compound 5 in which $R^6$ and $R^7$, together with the nitrogen atom to which they are attached, is piperazin-1-yl are those in which each of $R^1$, $R^2$, $R^4$, $R^5$, $R^8$, and $R^9$ is hydrogen; each of $R^1$, $R^2$, $R^4$, $R^5$ and $R^8$ is hydrogen and $R^9$ is cyano; each of $R^2$, $R^4$, $R^5$, and $R^8$ is hydrogen, and each of $R^1$ and $R^9$ is methoxy; each of $R^2$, $R^4$, $R^5$, and $R^8$ is hydrogen, and each of $R^1$ and $R^9$ is methyl; and each of $R^2$, $R^4$, $R^5$, and $R^8$ is hydrogen, and each of $R^1$ and $R^9$ is chloro. The biological activities for these embodiments are shown in the Appendix.

Still more examples of useful compounds are disclosed in the Appendix.

4.3 Synthesis of Compounds

The compound provided by the invention can be made using methods and materials known to those having ordinary skill in the art.

Starting from readily available compounds 6 and 7:

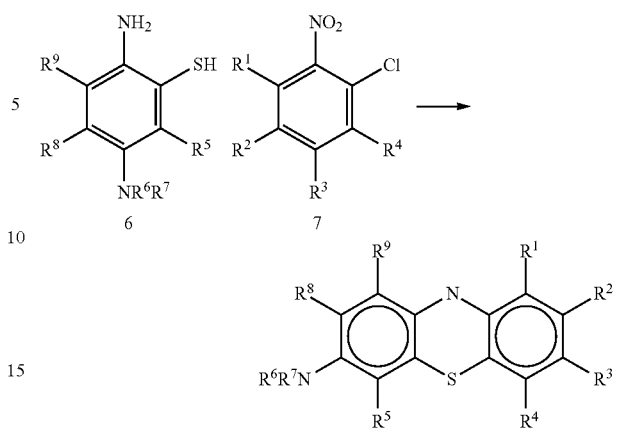

where $R^1$-$R^9$ have the meaning described above for Compound 1. Compounds where $R^3$ is oxo (e.g., Compound 2) can be made similarly from Compound 8:

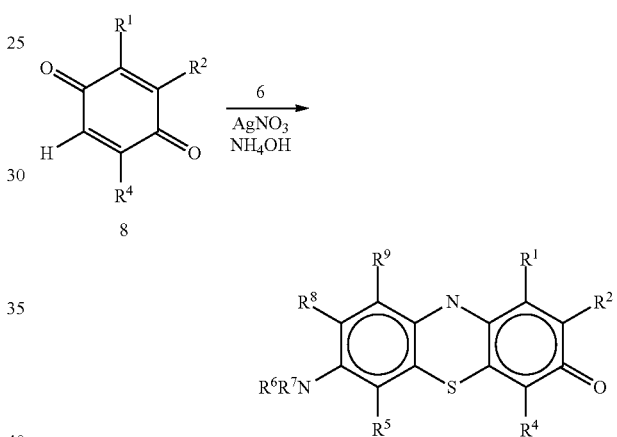

Still more methods for making compounds of the invention is provided hereinbelow.

4.4 Methods for Treating Viral Diseases

In another aspect, the present invention provides methods for treating a viral disease in a mammal afflicted with such disease. In some embodiments, the methods provided by the invention comprise administering to such mammal a therapeutically effective amount of a compound having the structure of Compound 1 above, including any of the compounds disclosed herein. The formulation and provision of suitable pharmaceutical compositions will be understood by those having ordinary skill in the art. Viruses that can be treated using the compounds of the invention include, but are not limited to, Flu, HCV, HIV, EBOV, MARB, DENV, VEEV, CHIKV, and WNV. In some embodiments, the virus is Ebola virus; in other embodiments, the virus is Marburg virus; and in still other embodiments, the virus is HIV. In one specific embodiment the present invention provides a methods for treating HIV as described herein in which the compound has the structure of Compounds 3, 4, and 5 above and the more specific embodiments thereof.

4.5 Compositions for, and Methods of, Treating Viral Infections

Compounds of the present invention can be administered in a variety of ways including enteral, parenteral and topical routes of administration. For example, suitable modes of administration include oral, subcutaneous, transdermal, transmucosal, iontophoretic, intravenous, intramuscular, intraperitoneal, intranasal, subdural, rectal, vaginal, and the like.

In accordance with other embodiments of the present invention, there is provided a composition comprising a compound described here, together with a pharmaceutically acceptable carrier or excipient. Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Mack Pub. Co., New Jersey (1991), which is incorporated herein by reference.

Pharmaceutical compositions of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the present invention may be administered orally, parenterally, sublingually, by inhalation spray, rectally, vaginally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid can be useful in the preparation of injectables.

Suppositories for rectal or vaginal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art.

While the compounds of the invention can be administered as the sole active pharmaceutical agent, they can also be used in combination with one or more other compound as described herein, or in combination with other agents used in the treatment or prevention of AD and related diseases, or both.

In addition, the compounds of the present invention can be used, either singly or in combination as described above, in combination with other modalities for preventing or treating AD and related diseases or disorders. Such other treatment modalities include without limitation, surgery, radiation, hormone supplementation, and diet regulation. These can be performed sequentially (e.g., treatment with a compound of the invention following surgery or radiation) or in combination (e.g., in addition to a diet regimen).

The additional active agents may generally be employed in therapeutic amounts as indicated by sources well known to those having ordinary skill in the art, e.g., the PHYSICIAN'S DESK REFERENCE (PDR) $53^{rd}$ Edition (1999), which is incorporated herein by reference, or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

In accordance with yet other embodiments, the present invention provides methods for treating or preventing AD or similar disorder in a human or animal subject in which an amount of a compound of the invention that is effective to at least ameliorate disease symptoms. Effective amounts of the compounds of the invention generally include any amount sufficient to detectably modulate AD using standard measures, by other methods known to those having ordinary skill in the art, or by detecting prevention or alleviation of symptoms in a subject afflicted with AD.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The prophylactically or therapeutically effective amount for a given situation can be readily determined by routine experimentation and is within the skill and judgment of the ordinary clinician.

For exemplary purposes of the present invention, a prophylactically or therapeutically effective dose will generally be from about 0.1 mg kg$^{-1}$d$^{-1}$ to about 100 mg kg$^{-1}$d$^{-1}$, preferably from about 1 mg kg$^{-1}$d$^{-1}$ to about 20 mg kg$^{-1}$d$^{-1}$, and most preferably from about 10 mg kg$^{-1}$d$^{-1}$ to about 10 mg kg$^{-1}$d$^{-1}$ of a compound of the present invention, which may be administered in one or multiple doses.

4.6 Examples 4.6.1 Synthesis of Compounds

The compounds of the present invention can be synthesized using techniques and materials known to those of skill in the art. Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Aspin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.)

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography ("TLC"), recrystallization, distillation, high-pressure liquid chromatography ("HPLC") and the like. Also, various techniques well known in the chemical arts for the identification and quantification of chemical reaction products, such as proton and carbon-13 nuclear magnetic resonance CH and $^{13}$C NMR), infrared and ultraviolet spectroscopy ("IR" and "UV"), X-ray crystallography, elemental analysis ("EA"). HPLC and mass spectroscopy ("MS") can be used for identification, quantitation and purification as well.

Although the schemes below illustrate specific starting materials and products, those having ordinary skill in the art will understand that many substitution patterns can be made using known methods and materials in combination with the teachings herein.

General Example I

Synthesis of 7-Amino-Substituted 3H-Phenothiazin-3-One Compounds 7-(Pyrrolidin-1-yl)-3H-phenothiazin-3-one

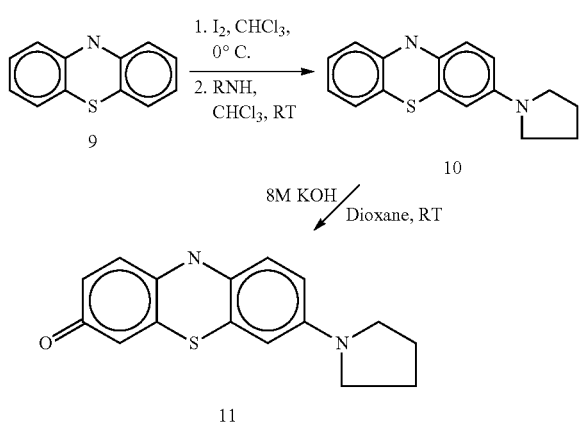

1. Synthesis of Phenothiazin-5-ium Tetraiodide Hydrate

Phenothiazine (9, 566 mg, 2.84 mmol) was dissolved in CHCl$_3$ (20 mL) and cooled to 5° C. To this solution was added a solution of I$_2$ (2.16 g, 8.51 mmol) dissolved in CHCl$_3$ (50 mL) was added over the course of 1 h. The reaction was stirred for 1 h more at 5° C. and a dark solid precipitated. The solid was stirred in ethyl ether for 1 h and filtered. The solid was dried under vacuum to give a quantitative yield of 2.00 g.

2. Synthesis of 3-Aminophenothiazin-5-ium Triiodide (10)

The phenothiazin-5-ium 1.65 g, 2.34 mmol) was dissolved in CHCl$_3$, and pyrrolidine (0.39 mL, 4.67 mmol) was added dropwise. The mixture was stirred at RT for 48 h. The solvent was decanted and washed three times with ethyl ether. The crude material was used without purification.

3. Synthesis of 7-(Pyrrolidin-1-yl-3H-phenothiazin-3-one (11)

The crude product isolated from the previous step was dissolved in 1,4-dioxane (10 mL), and to this solution was added an 8.0 m KOH solution (10 mL). The reaction was warmed to 70° C. with rapid stirring and the color of the solution became dark purple. After one hour, the reaction was allowed to cool to RT and the layers separated. The aqueous layer was washed with ethyl acetate and the combined organic layers were dried over MgSO$_4$, filtered and evaporated to give a residue. The residue was purified to give a dark colored product that was confirmed by LCMS.

General Example II

Synthesis of 1,9-Dimethylphenothiazin-5-ium

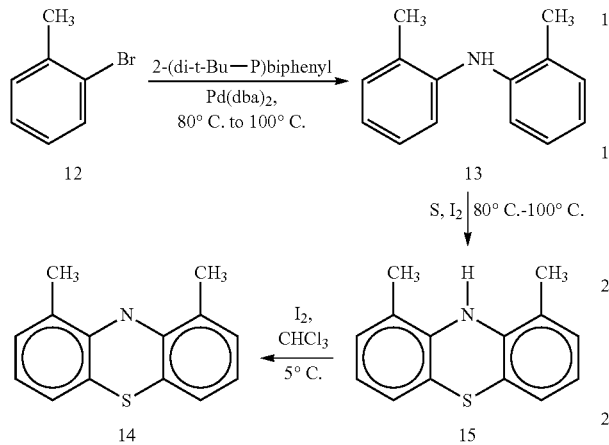

1. Synthesis of Di-ortho-tolylamine (13)

A round-bottom flask was heated, and then allow to cool to room temperature under argon. To the flask were added $Pd_2(dba)_3$ (1.39 g, 1.52 mmol, 1.0 mol %) or $Pd(dba)_2$ (1.38 g, 2.4 mmol, 1.4 mol %), 2-(di-tert-butylphosphino)biphenyl (1.09 g, 3.65 mmol, 2.4 mol %), 2-bromotoluene (12, 40 mL, 332.1 mmol) or 2-chlorotoluene (39 mL, 332.1 mmol), lithium amide (3.47 g, 151.1 mmol, 45 mol %), sodium t-butoxide 29.5 g, 297.7 mmol, 90 mol %), then toluene (150 mL). The reaction mixture was heated at 80° C. under argon overnight, then allowed to cool to room temperature. The resulting liquid was diluted with diethyl ether, and then filtered through a pad of celite. The resulting cocnentrte was filtered in vacuo and used in the next reaction without purification. The crude material was purified by column chromatography with hexane to give the product as white crystals with a yellow tint (23.4 g, 118.6 mmol, 72% yield).

2. Synthesis of 1,9-dimethyl-10H-phenothiazine (15)

To a reaction vessel were combined di(2-tolyl)amine (11.7 g, 59.3 mmol), elemental sulfur (3.9 g, 121.65 mmol, 2 eq.), crushed iodine (0.44 g, 1.73 mmol, 3 mol %) followed by o-dichlorobenzene (22 mL). Added an outlet to a dilute bleach solution (for hydrogen sulfide evolution) then put under argon. Refluxed at 180° C. for 4 h and removed solvent under reduced pressure. Purified by column chromatography with 2.0% ethyl acetate/98% hexane to obtain the desired product as white crystals (2 g, 8.8 mmol, 15% yield). Alternatively, the reaction was cooled to about 60° C. then hexane was added for extraction. Repeated hot hexane extractions of reaction until the product was no longer obtained in residue (about four times). Combined hexane extractions and concentrated in vacuo. Purified resulting residue either through repeated hot acetone/isopropanol crystallizations (or triturations) or flash column chromatography using 2% ethyl acetate/98% hexane to obtain product as white crystals (2.92 g, 12.8 mmol, 28% yield).

3. Synthesis of 1,9-Dimethylphenothiazin-5-ium (14)

1,9-dimethylphenothiazine (4.2026 g, 18.49 mmol) was dissolved in 130 mL of chloroform and crushed iodine (14.1 g, 55.55 mmol, 3 eqs.) dissolved in 520 mL of chloroform was added over 2 h. Once newly formed precipitate was filtered off or the solvent removed under vacuum, the resulting iodide salt was stirred with ether or hexane (sometimes overnight) to remove excess iodine then refiltered. After pumping down under vacuum, a brown precipitate was obtained as product (12.6 g).

General Example III

Synthesis of 1,9-Diethyphenthiazin-5-ium

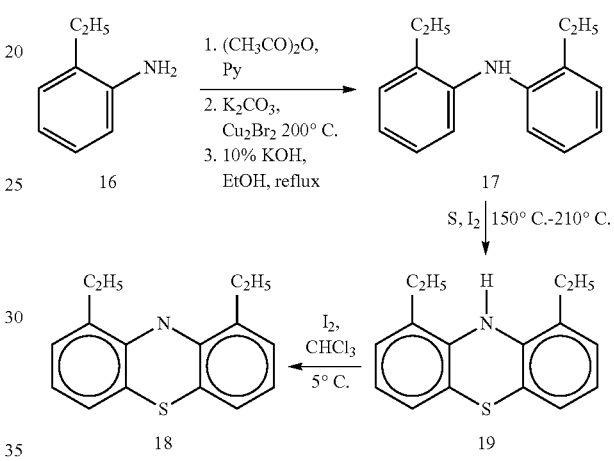

1. N-(2-Ethylphenyl)acetamide

To the stirred solution of commercially available ethyl aniline (16, 20.3 g, 167.5 mmol, 1 eq.) in anhydrous pyridine (90 mL), at zero degree, under argon was added acetic anhydride (32 mL, 335.04 mmol, 2 eq). After the addition, the resulting solution was stirred with warming to room temperature overnight. The reaction solution was cooled (0° C.), pH adjusted between 4 and 5 with 10% HCl, and extracted with ethyl acetate (2×500 mL). The combined organics were washed with brine, dried ($Na_2SO_4$), filtered and concentrated to provide the title compound as a white solid.

2. N,N-bis(2-Ethylphenyl)acetamide

The mixture of the N-(2-ethylphenyl)acetamide (7.35 g, 45.03 mmol), anhydrous $K_2CO_3$ (6.22 g, 45.03 mmol), copper(I) bromide (452.2 mg, 3.15 mmol) in 1-bromo-2-ethylbenzene was stirred and heated to 200° C. under argon for 48 h. After cooling the reaction mixture was poured into ice-$H_2O$ and extracted with ethyl acetate (2×500 mL), the combined organics were washed with brine, dried over anhydrous ($K_2CO_3$), filtered and concentrated to dryness. The crude product was purified using an ISCO machine using a ethyl acetate-hexane gradient to afford the product, N,N-bis(2-ethylphenyl)acetamide (8.1 g, 67%).

3. Bis(2-Ethylphenyl)amine (17)

The N,N-bis(2-ethylphenyl)acetamide (8.1 g, 30.30 mmol) and KOH (5 g), in EtOH (50 mL), was stirred and heated to reflux overnight. 20 hrs later additional KOH (10 g) was added, wth stirring to reflux continued for an additional 6 hrs. It was cooled, poured into H$_2$O (125 mL) and extracted with ethyl acetate (2×350 mL). The combined organics were washed with brine, dried (MgSO$_4$), filtered and concentrated to dryness, affording a dark red oil (5.8 g, 85%).

4. 1,9-Diethyl-10H-phenothiazine (18)

The bis(2-ethylphenyl)amine, sulfur and iodine in vial, containing an outlet for gaseous expulsion, was stirred in a preheated (150° C.) heating block for 15 min. The temperature was increased to 210° C., stirred and heated for an additional 45 min, and cooled. The dark mixture obtained was dissolved with 10% MeOH/dichloromethane, silica gel was added, and the soluation concentrated and purified on an ISCO machine using ethyl acetate-hexane gradient to afford the desired product (40%).

5. 1,9-Diethylphenothiazin-5-ium (7) (18)

This compound was prepared according the procedure by B. Wilson et. al, *Tetrahedron* 64 (2008), 3429-3436. To the solution of 1,9-diethyl-10H-phenothiazine (0.8 g, 3.13 mmol) in anhydrous chloroform (22 mL), at 5° C., was added a solution of iodine (2.4 g, 9.40 mmol) in CHCl$_3$ (55 mL) over a 1 h period. The resulting dark solution was stirred for an additional h at 5° C., monitored by TLC. After the disappearance of the starting material the cooling bath was removed, the solid precipitate was filtered, washed several times with chloroform, and dried to afford a very dark solid (1.02 g, 50%).

4.6.1.1 Preparation of 7-(Azepan-1-yl)-1,9-diethyl-3H-phenothiazin-3-one

To the solution of 1,9-diethylphenothiazin-5-ium tetraiodide hydrate (19), 0.240 g, 0.37 mmol) in CHCl$_3$ (10 mL) was added hexamethylenimine (85 µL, 0.75 mmol). The resulting mixture was stirred at room temperature for 3 h and concentrated to dryness to afford 3-(azepan-1-yl)-1,9-diethylphenothiazin-5-ium. The crude material was reacted in a manner similar to General Example III to obtain the desired product. The reaction mixture was diluted with dichloromethane, washed sequentially with brine, water, brine, dried (Na$_2$SO$_4$), filtered, concentrated and purified by flash chromatography using methanol-chloroform gradient to afford the title compound. MS (m/z):[M+H]±=367.

General Example IV

Tert-Butyl-3,7-dibromo-1,9-dichloro-10H-phenothiazine-10-carboxylate

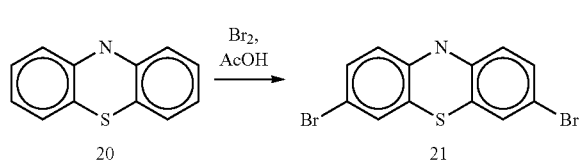

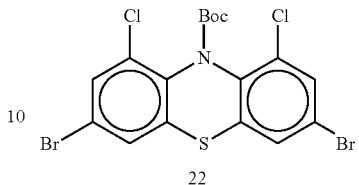

1. Synthesis of 3,7-Dibromo-10H-phenothiazine (21)

5.0 g (25 mmol) of Phenothiazine (20) was suspended in 200 mL of glacial AcOH. Then, 3.3 mL Br$_2$ (0.63 mol) in 200 mL of glacial was slowly added to the reaction mixture and stirred for 16 h at room temperature. The reaction was cooled with an ice bath and 6.30 g (50 mmol) of Na$_2$SO$_3$ was added to the reaction mixture. By adding a little water (3.0 mL), a deep-violet color formed within three hours. After the addition of a solution of 4.10 g (62 mmol) of KOH dissolved in water (1.0 L) a greenish solid forms which was washed with a little cold 2-propanol. The solid was recrystallized with 2-propanol to give 7.90 g (88%) as a green powder.

2. Synthesis of 3,7-Dibromo-1,9-dichloro-10H-phenothiazine

The 3,7-dibromophenothiazine (21, 6.25 g, 17.5 mmol) was dissolved in CHCl$_3$ (200 mL) and SO$_2$Cl$_2$ (3.13 mL, 38.5 mmol) was added dropwise over 15 min. The dark mixture was stirred at RT for 36 h. The mixture was then filtered and the solid washed with CHCl$_3$. The solid was collected and stirred in Et$_2$O and the resulting green solid was filtered off and dried under vacuum to give a quantitative yield of the desired product.

3. Synthesis of tert-Butyl 3,7-dibromo-1,9-dichloro-10H-phenothiazine-10-carboxylate (22)

The 3,7-dibromo-1,9-dichloro-10H-phenothiazine (10.00 g, 23.47 mmol) was suspended in CH$_3$CN (200 mL) and DMAP (2.87 g, 23.47 mmol) was added. The mixture was heated at reflux (near 85° C.) and Boc$_2$O (15.16 g, 70.41 mmol) dissolved in CH$_3$CN (50 mL) was added dropwise over 1 h. The reaction mixture became homogeneous and turned brown. The reaction was allowed to cool to RT and the solvent was evaporated. The residue was purified by flash silica gel chromatography to give a 95% yield.

General Example V

Synthesis of 1,9-Dicholorphenothiazin-5-ium

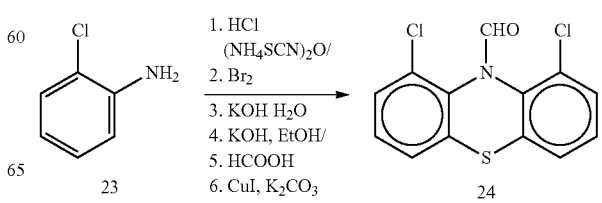

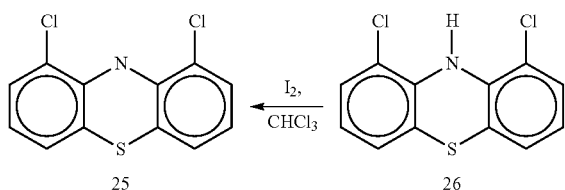

1. Synthesis of 1-(2-Chlorophenyl)thiourea

2-Chloroaniline (23, 10.52 mL, 100 mmol) was dissolved in conc. HCl (9 mL) followed by $H_2O$ (25 mL). The mixture was heated at reflux for 30 minutes then allowed to cool to rom temperature. To this solution was added $NH_4SCN$ (7.61 g, 100 mmol) and the mixture was heated at reflux overnight. The reaction was allowed to cool to room temperature and a solid formed. The water layer was decanted off and the solid was dissolved in $CH_2Cl_2$ and the organic layer was washed in brine. The organic layer was dried over $MgSO_4$, filtered and evaporated to give a residue, which was purified by flash silica gel chromatography.

2. Synthesis of 4-Chlorobenzo[d]thiazol-2-amine

The phenylthiourea (6.00 g, 32.16 mmol) was dissolved in $CHCl_3$ (150 mL) and cooled to 0° C. with an ice bath. To this mixture was added a solution of $Br_2$ (1.6 mL, 32.2 mmol) in $CHCl_3$ (100 mL) dropwise over 30 min. After the addition, the mixture was stirred at 0° C. for 1 h, then allowed to warm to rt. the reaction was refluxed for 3 h to 4 h than allowed to cool to room temperature. The organic solvent was removed and the residue was washed with sulfurous acid. The residue was then neutralized with liquid ammonia. The solid was filtered off, washed with watyer and recrystallized from EtOH.

3. Synthesis of 2-Amino-3-chlorobenzenethiol

The 4-chlorobenzo[d]thiazol-2-amine (2.00 g, 10.83 mmol) was combined with KOH (10.0 g, 178.2 mmol) and $H_2O$ (20 mL). The rsulting mixture was heated at 150° C. overnight. The solid became a thick paste overnight. After 24 h, the mixture was allowed to cool to room temperatureand diluted with $H_2O$. A solution of AcOH was added to bring the pH down to 4 to 5.

4. Synthesis of 2-Chloro-6-(2-chloro-6-nitrophenylthio)aniline

The 2-amino-3-chlorobenzenthiol (550 mg, 3.95 mmol) was dissolved in EtOH (10 mL) followed by KOH (220 mg, 3.95 mmol). To this mixture was added a solution of 1,2-dichloro-3-nitrobenzene (760 mg, 3.95 mmol) in EtOH (10 mL). The resulting reaction mixture was refluxed for 8 h to 12 h. The reaction was allowed to cool to room temperature and the residue was extracted with EtOAc and 1 mol $dm^{-3}$ $H_3PO_4$. The organic layer was dried over $MgSO_4$, filtered and evaporated to give a crude material. This crude material was purified by flash silica gel chromatography.

5. Synthesis of N-(2-Chloro-6-(2-chloro-6-nitrophenylthio)phenyl) formamide

A solution of 2-chloro-6-(2-chloro-6-nitrophenylthio) aniline (689 mg, 2.18 mmol) in formic acid (5 mL) was heated at reflux for 16 hours. The mixture was allowed to cool to room temperature and the solvent was evaporated. The residue was used without purification.

6. Synthesis of 1,9-Dichloro-10H-phenothiazine-10-carbaldehyde (24)

N-(2-Chloro-6-(2-chloro-6-nitrophenylthio)phenyl) formamide (750 mg, 2.18 mmol) was combined with CuI (85 mg, 0.45 mmol), $K_2CO_3$ (4.5 g, 32.56 mmol) and Xylenes (5.0 mL). The resulting mixture was heated at 150° C. for 12 h under argon. The reaction was allowed to cool to room temperature and was poured into ice water (50 mL) and extracted with EtOAc. The organic layer was ried over $MgSO_4$, filtered and evaporated to give a residue. (The residue contained both the 1,9-dichloro-10H-phenothiazine-10-carbaldehyde and 1,9-dichloro-10H-phenothiazine). The crude product was used without purification.

7. Synthesis of 1,9-Dichloro-10H-phenothiazine (26)

The mixture of the crude 1,9-dichloro-10H-phenothiazine-10-carbaldehyde was dissolved in acetone (8 mL) and a solution of KOH (330 mg, 5.88 mmol) in EtOH (5.0 mL) was added. The mixture was stirred for 12 h at room temperature and then was evaporated to dryness to give a residue. The residue extracted with EtOAc and washed with 1M $H_3PO_4$. The organic layers were combined and dried over $MgSO_4$, filtered and evaporated to give a residue. The residue was purified by flash silica gel chromatography to give 300 mg of a light yellow solid. LC/MS confirmed M+1=269.

8. Synthesis of 1,9-Dichlorophenothiazin-5-ium (25)

The 1,9-dichloro-10H-phenothiazine (200 mg, 0.746 mmol) was dissolved in $CHCl_3$ (8.0 mL) and $I_2$ (583 mg, 2.3 mmol) was added. The mixture was heated at 60° C. overnight. The reaction was allowed to cool to room temperature and the solvent was evaporated. The dark solid was used without further purification.

General Example VI

Synthesis of Fluorophenthiazin-3-one Derivatives

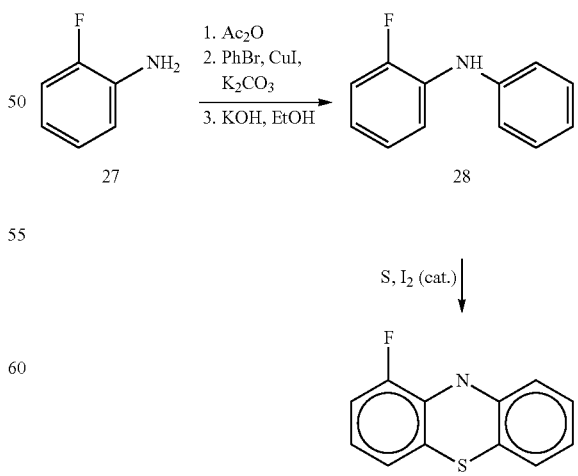

1. Synthesis of N-Acetyl-2-fluoroaniline

Acetic anhydride (57 mL, 0.6 mol) was added slowly, over approximately 40 min, to stirred 2-fluoroaniline (27, 55.7 g, 0.5 mol) under cooling (water bath) to maintain the reaction temperature at 60° C. to 70° C. After 10 hours more, the reaction mixture was poured into $H_2O$, the whole was extracted with ethyl acetate (2×300 mL). The combined organic extracts were washed with 5% aqueous $NaHCO_3$, brine, dried ($K_2CO_3$), filtered and concentrated to provide the title compound as a white solid (67.0 g, 88%).

2. Synthesis of N-Acetyl-2-fluorodiphenylamine

A mixture of the N-acetyl-2-fluoroaniline (61.2 g, 0.4 mol), anhydrous $K_2CO_3$ (55.2 g, 0.4 mol), CuI (38.0 g, 0.2 mol) and bromobenzene (234 mL, 1.0 mol) was stirred and heated at 175° C. to 180° C. under an Argon atmosphere for 72 h. After cooling the reaction mixture was poured into ice-$H_2O$ and extracted with ethyl acetate (2×200 mL), the combined organic extracts were washed with brine, dried over anhydrous $K_2CO_3$, filtered and concentrated to dryness. The obtained crude material was purified by flash chromatography (using ethyl acetate-hexane as an eluent) to afford the N-acetyl-2-fluorodiphenylamine (74.0 g, 81%).

3. Synthesis of 2-Fluorodiphenylamine (28)

A solution of the N-acetyl-2-fluoroldiphenylamine (57.2 g, 0.25 mol) in solution KOH (42 g, 75 mol)/EtOH (250 mL) was stirred and heated at 60° CC. for 1 h. Reaction progress was monitored by TLC. Solution was poured into $H_2O$. The mixture was extracted with ethyl acetate (2×100 mL). The combined organic layers were washed with brine, dried ($Na_2SO_4$), filtered and concentrated to dryness, gave title compound (46.8 g, 96%).

4. Synthesis of 1-Fluoro-10H-phenothiazine (29)

To 2-fluorodiphenylamine (3.66 g, 20 mmol), sulfur (1.22 g, 40 mmol) and iodine (1.52 g, 6 mmol) were added. Vial was charged with balloon for discharge. The hot block was preheated (150° CC.). The vial was heated on the hot block and after 15 min. temperature was increased to 210° CC., reaction mixture was stirred and heated for an additional 45 min. and cooled. The product was extracted by hexane and purified by flash chromatography (ethyl acetate-hexane as an eluent) to afford the desired product (2.6 g, 60%).

7-(dimethylamino)-1-fluoro-phenothiazin-3-one

1. Synthesis of 3,7-Dibromo-1-fluoro-10H-phenothiazine

1-Fluoro-10H-phenothiazine (1.34 g, 6.2 mmol) was dissolved in acetic acid (10 mL) and stirred at room temperature as a solution of bromine (2.96 g, 0.95 mL, 18.5 mmol) in acetic acid (50 mL) was added. The mixture was allowed to stir overnight at this condition. To this mixture sodium sulfite $Na_2SO_3$ (1.56 g, 12.4 mmol) and water (2 mL) were added. The mixture was stirred at room temperature for 3 h. After that reaction mixture was poured into 100 mL of ice-water contained NaOH (1.0 g, 25 mmol). The mixture was stirred overnight and filtered, gave light green solid (1.70 g, 73%).

2. Synthesis of 3,7-Dibromo-1-fluoro-10-Boc-phenothiazine 3,7-Dibromo-1-fluoro-10H-phenothiazine (1.7 g, 4.5 mmol) was suspended in $CH_3CN$ (20 mL) and (Boc)$_2$O (2.94 g, 13.5 mmol) and DMAP (0.55 g, 4.5 mmol) were added. The mixture was warmed to 50° C. After 5 min. starting material was dissolved in solvent, $CO_2$ was eliminated and solid material formed. After 2 h the reaction mixture was cooled to room temperature. The solid was filtered off and dried on air (1.71 g, 80%).

3. Synthesis of 3-Dimethylamino-1-fluoro-7-bromo-10-Boc-phenothiazine

To a stirred solution of 3,7-dibromo-1-fluoro-10-Boc-phenothiazine (8) (475 mg, 1 mmol) in touene (10 mL) Pd(dba)$_2$ (28.9 mg, 0.05 mmol), BINAP (22.5 mg, 0.035 mmol), $Cs_2CO_3$ (652 mg, 2 mmol) and dimethylamine (0.6 mL, 1.2 mmol) were added. The mixture was refluxed for 24 h. After that reaction mixture was filtered, solvent was removed under vacuum. Product was used without additional purification.

4. Synthesis of 3-Dimethylamino-7-tert-butoxy-1-fluoro-10-Boc-phenothiazine

To a solution 3-dimethyl-amino-1-fluoro-7-bromo-10-Boc-phenothiazine (200 mg) in toluene (10 mL) sodium tert-butoxide (115 mg, 1.2 mmol), sodium hydride (60% dispersion in mineral oil) (50 mg, 1.2 mmol), Pd(dba)$_2$ (5.8 mg, 0.01 mmol) and BINAP (6.3 mg, 0.01 mmol) were added. The reaction mixture was stirred at 90° C. for 24 h. Solvent was removed under vacuum.

5. Synthesis of 3-Dimethylamino-1-fluorophenothiazin-3-one

To a solution 3-dimethylamino-7-tert-butoxy-1-fluoro-10-Boc-phenothiazine (150 mg) in dichloromethane (10 mL) HCl (3 mL, 4 A/solution in 1,4-dioxane) was added. The reaction mixture was stirred at room temperature for 2 h. After that solution was neutralized with KOH (0.2 mL, 8 M solution in 1,4-dioxane). Reaction mixture was stirred for 1 h. Solvent was removed under vacuum. Product was purified by flash chromatography and prep-Plate.

1,9-Difluoro-10H-phenothiazine

The named compound was made using the protocol described above, using 1-bromo-2-fluorobenzene instead of bromobenzene.

1,9-difluoro-7-(pyrrolidin-1-yl)-3H-phenothiazin-3-one

The named compound was made using the protocol described above.

Example 43

1,9-difluoro-7-(pyrrolidin-1-yl)-3H-phenothiazin-3-one

The named compound was made as described below, using the general protocol described above.

1. Synthesis of N-acetyl-o-trifluoromethylaniline

Commercial o-trifluoromethylaniline (13.5 g, 83.9 mmol) was dissolved in acetic anhydride (55 mL, 580.0 mmol) and stirred at room temperature for 1 h. Then the reaction mixture was poured into $H_2O$, the whole was extracted with ethyl acetate (2×300 mL). The combined organic extracts were washed with 5% aqueous NaHCO$_3$, brine, dried (K$_2$CO$_3$), filtered and concentrated to provide the title compound as a white solid (15.7 g, 92%).

2. Synthesis of N-acetyl-2-trifluoromethyldiphenylamine a mixture of the N-acetyl-o-trifluoromethyl-aniline (6.1 g, 30.0 mmol), anhydrous K$_2$CO$_3$ (4.1 g, 30.0 mmol), CuI (210 mg, 1.1 mmol) and bromobenzene (16 mL, 160 mmol) was stirred and heated at 175° C. to 180° C. under an Ar atmosphere for 48 h. After cooling the reaction mixture was poured into ice-H$_2$O and extracted with ethyl acetate (2×200 mL), the combined organic extracts were washed with brine, dried over anhydrous K$_2$CO$_3$, filtered and concentrated to dryness. The obtained crude material was purified by flash chromatography (using ethyl acetate-hexane as an eluent) to afford the N-acetyl-2-trifluoromethyldiphenylamine (5.4 g, 64%).

3. Synthesis of 2-trifluoromethyldiphenylamine a solution of the N-acetyl-2-trifluoromethyldiphenylamine (3.5 g, 12.5 mmol) in 10% KOH (2 g, 36 mmol) and EtOH (20 mL) was stirred and reflux for 6 h, then poured into H$_2$O. The mixture was extracted with ethyl acetate (2×100 mL). The combined organic layers were washed with brine, dried (Na$_2$SO$_4$), filtered and concentrated to dryness, gave dark red oil (2.5 g, 85%).

4. Synthesis of 1-trifluoromethyl-10H-phenothiazine to a 2-trifluoromethyldiphenylamine (1.1 g, 4.6 mmol), sulfur (295 mg, 9.2 mmol) and iodine (328 mg, 1.29 mmol) were added. Vial was charged with balloon for discharge. The hot block was preheated (150° C.). The vial was heated on the hot block and after 15 min. temperature was increased to 210° C., reaction mixture was stirred and heated for an additional 45 min. and cooled. The dark solid material was dissolved in mixture methanol/chloroform and purified by flash chromatography (ethyl acetate-hexane as an eluent) to afford the desired product (450 mg, 36%).

Synthesis of 1-Cyanophenothiazine

Prepared 1-cyanophenothiazine as described in the literature starting from 2-aminobenzenethiol (2.1 mL, 2.46 g, 20 mmol), 2,3-difluorobenzonitrile (1.9 mL, 2.83 g, 20 mmol), and sodium hydride (1.09 g, 27.3 mmol) in 10 mL of DMF. After crystallizing from dichloromethane-ethanol, 1-cyanophenothiazine was obtaind as a dark yellow powder (1.34 g, 6 mmol, 30° C. yield).

Synthesis of 1-Cyanophenothiazin-5-ium

Procedure the same as above, but with 1-cyanophenothiazine instead of 1,9-dimethylphenothiazine.

Other Examples

The following compounds were made using the general procedures described above.
1. 7-[Bis(2-methoxyethyl)amino]phenothiazin-3-one
2. 7-Pyrrolidin-1-ylphenothiazin-3-one
3. 7-(Diethylamino)phenothiazin-3-one
4. 7-(Dimethylamino)phenothiazin-3-one
5. 7-(Azetidin-1-yl)phenothiazin-3-one
6. 7-[2-Methoxyethyl(methyl)amino]phenothiazin-3-one
7. 7-(4-Methylpiperazin-1-yl)phenothiazin-3-one:
8. 7-(4-Isopropylpiperazin-1-yl)phenothiazin-3-one
9. 7-Morpholinophenothiazin-3-one
10. 7-(4-Methylsulfonylpiperazin-1-yl)phenothiazin-3-one
11. 1-(7-oxophenothiazin-3-yl)piperidine-4-carboxamide
12. tert-Butyl 4-(7-oxophenothiazin-3-yl)piperazine-1-carboxylate
13. 7-piperazin-1-ylphenothiazin-3-one
14. 7-(dimethylamino)-1,9-dimethyl-phenothiazin-3-one
15. 1,9-dimethyl-7-(4-methylpiperazin-1-yl)phenothiazin-3-one
16. 7-[bis(2-methoxyethyl)amino]-1,9-dimethyl-phenothiazin-3-one
17. 1,9-dimethyl-7-morpholino-phenothiazin-3-one
18. tert-butyl 4-(1,9-dimethyl-7-oxo-phenothizin-3-yl)piperazine-1-carboxylate
19. 1,9-Dimethyl-7-piperazin-1-yl-phenothiazin-3-one
20. 1,9-Dimethyl-7-pyrrolidin-1-yl-phenothiazin-3-one
21. tert-butyl 4-(1,9-Dimethyl-7-oxo-phenothiazin-3-yl)-1,4-diazepane-1-carboxylate
22. 7-(Azepan-1-yl)-1,9-dimethyl-phenothiazin-3-one
23. 7-(Azetidin-1-yl)-1,9-dimethyl-phenothiazin-3-one
24. 7-(4-Isopropylpiperazin-1-yl)-1,9-dimethyl-phenothiazin-3-one
25. 1,9-Dimethyl-7-(4-methylsulfonylpiperazin-1-yl)phenothiazin-3-one
26. 1-(1,9-Dimethyl-7-oxo-phenothiazin-3-yl)piperidine-4-carboxamide:
27. 1,9-Dimethyl-7-[4-(trifluoromethylsulfonyl)piperazin-1-yl]phenothiazin-3-one
28. 7-(4-Isopropylsulfonylpiperazin-1-yl)-1,9-dimethyl-phenothiazin-3-one
29. 7-(4,4-Difluoro-1-piperidyl)-1,9-dimethyl-phenothiazin-3-one
30. 1-(1,9-Dimethyl-7-oxo-phenothiazin-3-yl)piperidine-4-carboxamidine
31. 7-(1,4-Diazepan-1-yl)-1,9-dimethyl-phenothiazin-3-one
32. 7-(Azepan-1-yl)-1,9-diethyl-phenothiazin-3-one
33. 1,9-Dichloro-7-pyrrolidin-1-yl-phenothiazin-3-one
34. 1,9-Dichloro-7-(dimethylamino)phenothiazin-3-one
35. N-tert-butyl-4-(1,9-Dichloro-7-oxo-phenothiazin-3-yl)piperazine-1-carboxamide
36. 7-[bis(2-Methoxyethyl)amino]-1,9-dichloro-phenothiazin-3-one
37. 4-(1,9-Dichloro-7-oxo-phenothiazin-3-yl)-N,N-dimethyl-piperazine-1-sulfonamide
38. 1,9-Dichloro-7-[4-(trifluoromethylsulfonyl)piperazin-1-yl]phenothiazin-3-one
39. tert-butyl 4-(1,9-Dichloro-7-oxo-phenothiazin-3-yl)piperazine-1-carboxylate
40. 1,9-Dichloro-7-piperazin-1-yl-phenothiazin-3-one
41. 7-(dimethylamino)-1-fluoro-phenothiazin-3-one
42. 1,9-Difluoro-7-pyrrolidin-1-yl-phenothiazin-3-one
43. 7-(Dimethylamino)-1-(trifluoromethyl)phenothiazin-3-one
44. 7-(1-Piperidyl)-9-(trifluoromethyl)phenothiazin-3-one
45. 7-oxo-3-pyrrolidin-1-yl-phenothiazine-1-carbonitrile
46. 7-[bis(2-methoxyethyl)amino]-3-oxo-phenothiazine-1-carbonitrile
47. 1,9-Dimethoxy-7-(4-methylpiperazin-1-yl)phenothiazin-3-one
48. 1,9-Dimethoxy-7-pyrrolidin-1-yl-phenothiazin-3-one
49. 1-tert-butyl-7-Pyrrolidin-1-yl-phenothiazin-3-one

4.6.2 Biological Activity of Compounds

4.6.2.1 Respiratory Viruses

The activities of compounds of the invention were determined for the following viruses using the protocol below:
- Corona Virus on MRC5 Cells
- Influenza Virus A on MDCK Cells
- Respiratory Syncytial Virus on HEp2 cells
- Adenovirus serotype 5 on A549 cells
- Human Rhinovirus on H1Hela Cells
- Herpes Simplex Virus 1 on Vero cells Virus was grown in the presence of four dilutions (10 µM, 2 µM, 0.4 µM and 0.08 µM) of the chemical compound tested with two controls using standard methods and materials for the relevant virus. The infected cell extract was collected using known methods, and the infectious virus concentration was determined using standard techniques.

Each well was titrated by $TCID_{50}$. Four serial dilutions in quadruplicate required to determine the titer of each well. To assay 36 replicates as directed, one hundred eight (108) 96-well plates is required. Each drug was tested at four dilutions against one virus will require $TCID_{50}$ titers of 18 sample wells.

4.6.2.2 Monkey Pox Virus

Compounds of the invention were tested for actvitiy against monkey pox virus using the following protocol:
1. Infected cells with target dose of 100 PFU/well MPXV.
2. One hour later, removed the virus solution and wash cells with media and aspirated.
3. Added serial half-log dilutions of compounds in methyl cellulose to triplicate wells; methyl cellulose is semi-solid media which contains virus in one location, so only the adjacent cells are infected. Each plate included a positive control of virus only wells (triplicate), with methyl cellulose overlay.
4. Four days later, removed the media from wells and added crystal violet to stain the cells.
5. After 20 min to 30 min later, washed the cells with $ddH_2O$ and dried.
6. Counted the plaques.
7. Compared plaque numbers of compound wells with the plaque numbers in virus only wells and determined the difference (percentage) of inhibition vs. protection.

4.6.2.3 Marburg Virus

Compounds of the invention were tested against Marburg virus using the following protcol:

Dimethylsulfoxide (DMSO) in 5 mM concentration was used as a solvent for the compounds and as a control. The compounds tested were stored under argon. Each compound was provided in a vial. The experiments were performed on 24-well plate.

Incubation of Compounds With Cells.

Day 0: Plated Vero cells at $1\times10^5$ cells/well in a 1 mL volume of medium (24-well plate), and incubated overnight.

Day 1:
1. Following sterile procedure, diluted each of the four compound stocks in DMSO to concentrations 100-fold greater than will be used in the treatment wells.
2. Further diluted the DMSO stocks 1:100 in EMEM with 10% FBS/Pen/Strep to generate treatments containing 1% DMSO. To generate DMSO control media, diluted DMSO (no compound) to 1% in EMEM with 10% FBS/Pen/Strep.
3. Aspirated the media in cell plates and added 1 mL of compound or control to the appropriate wells.
4. Incubated plate overnight.

Day 2:
1. Dilute virus: Diluted MARV to a concentration of $1\times10^6$ pfu/mL EMEM with 10% FBS/Pen/Strep.
2. Infection: Removed media from wells and applied 100 µL diluted virus to each well, except mock-infected well. Applied 100 µL EMEM with 10% FBS to the mock-infected well. Incubated the plate for 1 h at 37° C., rocking the plate gently every 15 min to prevent the cell monolayer from drying out.
3. Wash cells and add compound: After the one-hour infection period, aspirated the virus from the wells and add 1 mL PBS to each well. Aspirated the PBS and immediately added 1 mL diluted compound to the appropriate wells. The DMSO control and mock-infected wells received 1 mL of the DMSO control media.
4. Critical Treatments:
   (a) Compound Treatment Wells
   (b) DMSO control media+virus
   (c) DMSO control media no virus (Mock)
5. Incubated the plates at 37° C. under 5% $CO_2$ for 72 h.

Day 3: Removed as much media as possible from each well and stored at −80° C.

Determination of Plaques.

Day 0: Seeded 6-well plates with $2.5\times10^5$ Vero cells/well in 2 mL volumes of medium. Incubated overnight.

Day 1:
1. In deep-well 96-well plates prepared six 1:10 serial dilutions of supernatants from each well beginning with 1:10 and ending with 1:6 in 500 µL volumes EMEM with 2% FBS:
   (a) Diluted 60 µL undiluted supe into 540 µL EMEM with 2% FBS=1:1.
   (b) Diluted 60 µL of the 1:1 supe into 540 µL EMEM with 2% FBS=1:2.
   (c) Diluted 60 µL of the 1:2 supe into 540 µL EMEM with 2% FBS=1:3.
   (d) Diluted 60 µL of the 1:3 supe into 540 µL EMEM with 2% FBS=1:4
   (e) Diluted 60 µL of the 1:4 supe into 540 µL EMEM with 2% FBS=1:5
   (f) Diluted 60 µL of the 1:5 supe into 540 µL EMEM with 2% FBS=1:6
2. Prepared 2% agarose and place in a 37° C. water bath to prevent the solution from solidifying. Prewarm 2×EMEM in a 37° C. water bath.
   (a) Volume of agarose needed=12 mL per undiluted supe sample+extra.
   (b) Volume of 2×EMEM needed is the same.
3. Removed culture supernatant from plated cells and add 200 µL of diluted culture supernatant in duplicate to appropriate wells, according to plate diagram.
4. Incubated each plate for 1 h at 37° C. under 5% $CO_2$, rocking the plate gently every 15 minute.
5. After plates had incubated for 1 h, combined the 2% agarose with the 2×EMEM and mixed well. Gently applied 2 mL overlay to each well without removing the inoculum and swirled the plate gently to mix the inoculum in with the overlay. Repeated this process to apply overlays to each plate.
6. Allowed the overlays to solidify at room temperature for 1 h.
7. Incubated the plates for 5 d at 37° C. under 5% $CO_2$.
8. Stained the cells using a secondary overlay containing neutral red and incubate for 24 h.
9. Quantified the plaques in each well.

4.6.2.4 Influenza Virus

Compounds of the invention were tested for activity against Influenza virus using the following protocol:

1. MDCK (Madin-Darby canine kidney) cells were plated in three 96-well plates ($6\times10^4$ per well) and cultured overnight. The next day the cells were inspected with a microscope to document the confluence. The required amount of wells were infected with the fowl plaque virus (Influenza A/H7N7/Bratislava/1979) with an MOI of 1 (assuming duplication of cells over night to generate $1.2\times10^5$ PFU/well). Infection was performed with 200 μL of virus suspension. All three plates were treated identically and served as triplicates. On each plate was one well with one concentration of substance, three wells with the highest concentration of DMSO that is used on the plate, and three wells with the lowest concentration of DMSO that is on the plate. In addition there were three infected wells that were cultured with cell culture medium without additional substance. There also were 12 wells on every plate that were not infected and served as controls for the cpe determination and for the neutral red staining.
2. Substances were diluted before cells were infected and plates in 96-well plates so that they could easily be plated on the infected cells.
3. Infection was performed for 30 min at 37° C. in a cell culture incubator.
4. After infection the cells were washed once with infection-PBS. During washing the cell monolayer was inspected with a microscope, and damaged monolayers were excluded from testing. Uninfected wells were mock infected with infection-PBS and also inspected visually.
5. The pattern of substances on every individual plate was marked on the top of the plate and on a scheme.
6. An aliquot of 250 μL of diluted substance was used and cells were incubated for 16 h. After incubation time the cell monolayer was again inspected and cpe was monitored and recorded.
7. Supernatants of the first plate were transferred to a 96-well ELISA-plate and kept cool for titration, which wass performed later the same day.
8. Cells of this plate were washed carefully with PBS again inspected at the microscope and then stained with neutral red (which is staining the living cells) for 3 hours at 37° C. (neutral red is used at the concentration 1 mg/20 mL MEM; 200 μL/well.
9. In the meantime the dilutions for the titration were generated in a 96-well plate by diluting the supernatants 1:10. A 100 μL aliquot of undiluted supernatant and five dilutions (from $10^{-1}$ to $10^{-5}$ were used to infect 24-wells of MDCK monolayers of cells. This means that at this time point we only titrate one unique copy of every tested substance. The other three plates were immediately frozen at −70° C. and stored until titration.
10. The neutral red staining was stopped by washing the monolayer three times very carefully with PBS and the plate was dried on cellulose to eliminate residual PBS.
11. The neutral red was dissolved from the cells by using Ethanol/acidic acid for 15 min on a plate rocking platform.
12. The Ethanol/acidic acid was transferred to an Elisa-plate and measured at 570 nm in an Elisa-reader.
13. The percentage of live cells was calculated setting the non-infected cells to 100%.

Compounds having useful activities against influenza as determined by this assay, viz. compounds having values of $IC_{50}\leq30$ μmol include but are not limited to: 7-[bis(2-methoxyethyl)amino]-3H-phenothiazin-3-one, 7-(pyrrolidin-1-yl)-3H-phenothiazin-3-one, 7-(diethylamino)-3H-phenothiazin-3-one, 7-(pyrrolidin-1-yl)-3-oxo-3H-phenothiazine-9-carbonitrile, 1,9-dimethyl-7-(4-methylpiperazin-1-yl)-3H-phenothiazin-3-one, 7-[bis(2-methoxyethyl)amino]-1,9-dimethyl-3H-phenothiazin-3-one, 7-(dimethylamino)-1-(trifluoromethyl)-3H-phenothiazin-3-one, 1,9-dimethyl-7-(morpholin-4-yl)-3H-phenothiazin-3-one, 1,9-dimethoxy-7-(4-methylpiperazin-1-yl)-3H-phenothiazin-3-one, 1,9-dimethoxy-7-(pyrrolidin-1-yl)-3H-phenothiazin-3-one, 7-[bis(2-methoxyethyl)amino]-3-oxo-3H-phenothiazine-1-carbonitrile, 7-(dimethylamino)-1,9-dimethyl-3H-phenothiazin-3-one, 1,9-dichloro-7-(pyrrolidin-1-yl)-3H-phenothiazin-3-one, and 1,9-dimethyl-7-[4-(propan-2-yl)piperazin-1-yl]-3H-phenothiazin-3-one.

4.6.2.5 Ebola Virus

Compounds of the invention were tested for activity against Ebola virus using the following protocol:

Concentration of Compound 10 mM DMSO stock. Day 0:

Vero cells were plated at $1\times10^5$ cells/well in a 1 mL volume of medium (24-well plate), and incubate overnight.

Day 1: Compound Dilutions

1. Following sterile procedure, diluted each of the four compound stocks in DMSO to concentrations 100-fold greater than will be used in the treatment wells.
2. Further diluted the DMSO stocks 1:100 in EMEM with 10% FBS/Pen/Strep to generate treatments containing 1% DMSO. To generate DMSO control media, diluted DMSO (no compound) to 1% in EMEM with 10% FBS/Pen/Strep.
3. Aspirated the media in cell plates and add 1 mL of compound or control to the appropriate wells.
4. Incubated plate overnight.

Day 2:

1. Diluted virus.: Diluted EBOV to a concentration of $1\times10^6$ PFU/mL Eagle's Minimum Essential Medium (EMEM) with 10% FBS/Pen/Strep.
2. Infection.: Removed media from wells and applied 100 μL diluted virus to each well, except mock-infected well. Applied 100 μL) EMEM with 10% FBS to the mock-infected well. Incubated the plate 1 h at 37° C., rocking the plate gently every 15 min to prevent the cell monolayer from drying out.
3. Washed cells and added compound. After the 1 h infection period, aspirated the virus from the wells and added 1 mL PBS to each well. Aspirated the PBS and immediately added 1 mL diluted compound to the appropriate wells. The DMSO control and mock-infected wells received 1 mL of the DMSO control media.
4. Critical Treatments:
   (a) Compound Treatment Wells
   (b) DMSO control media+virus
   (c) DMSO control media no virus (Mock)
5. Incubated the plates: Incubated the plates at 37° C. under 5% $CO_2$ for 72 h.

Day 3:

Removed the Supernatant from Infected Plates:

Removed as much media as possible from each well and stored at −80° C.

Plaque Assay:

Day 0:

1. Seeded 6-well plates with $2.5\times10^5$ Vero cells/well in 2 mL volumes of medium. Incubated overnight.

Day 1:

1. In deep-well 96-well plates prepared six 1:10 serial dilutions of supernatants from each well beginning with 1:10 and ending with 1:$10^6$ in 500 μL volumes of EMEM with 2% FBS:
   (a) Diluted 60 μL undiluted supe into 540 μL EMEM with 2% FBS=1:$10^1$.
   (b) Diluted 60 μL of the 1:$10^1$ supe into 540 μL EMEM with 2% FBS=1:$10^2$.
   (c) Diluted 60 μL of the 1:$10^2$ supe into 540 μL EMEM with 2% FBS=1:$10^3$.
   (d) Diluted 60 μL of the 1:$10^3$ supe into 540 μL EMEM with 2% FBS=1:$10^4$
   (e) Diluted 60 μL of the 1:$10^4$ supe into 540 μL EMEM with 2% FBS=1:$10^5$
   (f) Diluted 60 μL of the 1:$10^5$ supe into 540 μL EMEM with 2% FBS=1:$10^6$
2. Prepared 2% agarose and placed in a 37° C. water bath to prevent the solution from solidifying. Prewarmed 2×EMEM in a 37° C. water bath.
   (a) Volume of agarose needed=12 mL per undiluted supe sample+extra.
   (b) Volume of 2×EMEM needed is the same.
3. Removed culture supernatant from plated cells and added 200 μL of diluted culture supernantant in duplicate to appropriate wells, according to plate diagram.
4. Incubated each plate for 1 h at 37° C. under 5% $CO_2$, rocking the plate gently every 15 min.
5. After plates had incubated for 1 h, combined the 2% agarose with the 2×EMEM and mixed well. Gently applied 2 mL overlay to each well without removing the inoculum and swirled the plate gently to mix the inoculum in with the overlay. Repeated this process to apply overlays to each plate.
6. Allowed the overlays to solidify at room temperature for 1 h.
7. Incubated the plates for 5 d at 37° C. under 5% $CO_2$.
8. Stained the cells using a secondary overlay containing neutral red and incubated for 24 h.
9. Quantified the plaques in each well.

Compounds having useful activities against ebola virus as determined by this assay, viz. compounds having values of $IC_{50}$≤30 μmol include but are not limited to: 7-(pyrrolidin-1-yl)-3H-phenothiazin-3-one, 7-(dimethylamino)-1-(trifluoromethyl)-3H-phenothiazin-3-one, and methane tert-butyl 4-(1,9-dimethyl-3-oxo-3H-phenothiazin-7-yl)piperazine-1-carboxylate.

4.6.2.6 Dengue, Easter Equine Encephalitis, Venezuelan Equine Encephalitis, Western Equine Encephalitis, West Nile, and Chikungunya Viruses Compounds of the invention were tested for activity against Dengue, Easter Equine Encephalitis, Venezuelan Equine Encephalitis, Western Equine Encephalitis, West Nile, and Chikungunya Viruses using the following protocol:

1. The Set test sample was set up in ten-fold dilutions across a 96-well plate. A mixture of 270 μL HBSS with HEPES and 2% FBS with Pen/Strep or complete media 2% FBS was added to each well. To the first well in each row 30 μL of test sample was introduced (i.e, a 1:10 dilution) and mixed. A 30 μL aliquot was tranferred from the first well to next well, and so on. Dilutions out to well #9 were made to provide a range of dilutions from 10" to $10^{-9}$. Be sure to discard tips between transfers.
2. Once dilutions were ready the plates were labeled with sample number and dilutions (plates can be labeled at any time prior to infection). Each dilution was plated on two wells. If plating dilutions $10^{-1}$ to $10^{-9}$, requires three plates per sample.
3. The media was removed from six-well plates by inverting over a dispo pan containing microchem disinfectant. Then 100 μL was added to each well of virus dilution. A duplicate was done to obtain an average. The plates were incubated at 37° C., 5% $CO_2$ for 1 h with occasional rocking (approximately every 15 min).
4. Preparation of media and agarose for overlay. Final concentration 1×EMEM, 10% FBS, 1% Pen/Strep, 0.1% gentamycin, in a 0.6% agarose solution (see cell culture overlay without neutral red chart). Added about 2 mL of overlay to each well and returned to the incubator. (It is not necessary to allow to solidify prior to placing in the incubator.) Incubated overnight at 37° C., 5% $CO_2$.
5. Next day: The resulting plaques were visualized with Neutral Red. A media/agarose overlay was prepared as above with 4% neutral red solution added to the media/agarose overlay as prepared in Step 4 (see cell culture overlay with neutral red overlay chart). Added about 2 mL ml per well.
6. Incubated the plates overnight at 37° C., 5% $CO_2$.
7. Counted plaques.

Compounds having useful activities against one or more of the above-described viruses as determined by these assays, viz. compounds having values of $IC_{50}$≤30 μmol, include but are not limited to: 7-(pyrrolidin-1-yl)-3H-phenothiazin-3-one, 7-(diethylamino)-3H-phenothiazin-3-one, 7-[bis(2-methoxyethyl)amino]-1,9-dimethyl-3H-phenothiazin-3-one, 1,9-dimethoxy-7-(pyrrolidin-1-yl)-3H-phenothiazin-3-one, methane tert-butyl 4-(1,9-dimethyl-3-oxo-3H-phenothiazin-7-yl)piperazine-1-carboxylate, and 7-(azetidin-1-yl)-3H-phenothiazin-3-one.

4.6.2.7 HIV Virus

H9 cells were obtained from the AIDS Research and Reference Reagent Program. A chronically infected cell population was generated by infection with HIV-1 SK-1 (references 1 & 2 below) and long term culture. Cells wer maintained under standard culture conditions in RPMI 1640 supplemented with 15% fetal bovine serum (heat inactivated), 2 mm L-glutamate, 100 U $mL^{-1}$ penicillin and 100 μg $mL^{-1}$ streptomycin. Cultures are maintained in such a way as to ensure exponential growth of the populations. At the time of the assay cells are collected by centrifugation and counted by hemacytometer. If cell viability by Trypan Blue dye exclusion is less than 90% the assay is terminated. The cells are adjusted to $3\times10^5$ cells $mL^{-1}$ and 100 μL placed in 96-well plates with 100 μL media containing the test compound. Cultures are incubated for 3 d and supernatants harvested. Compound toxicity is determined by MTS dye reduction. Virus expression is measured by supernatant reverse transcriptase activity and subsequent determination of supernatant virus infectivity by MAGI assay.

Reverse Transcriptase Activity Assay

A microtiter plate-based reverse transcriptase (RT) reaction was utilized (Buckheit et al., *AIDS Research and Human Retroviruses* 7:295-302, 1991). Tritiated thymidine triphosphate ($^3$H-TTP, 80 Ci $mmol^{-1}$, NEN) was received in 1:1 $dH_2O$:Ethanol at 1 mCi $mL^{-1}$. Poly rA:oligo dT template:primer (Pharmacia) was prepared as a stock solution by combining 150 μLpoly rA (20 mg $mL^{-1}$ with 0.5 mL oligo dT (20 U $mL^{-1}$) and 5.35 mL sterile $dH_2O$ followed by aliquoting (1.0 mL) and storage at −20° C. The RT reaction buffer was prepared fresh on a daily basis and consists of 125 μL 1.0 M EGTA, 125 μA $dH_2O$, 125 μL 20% Triton X100, 50 μA 1.0 M Tris (pH 7.4), 50 μL 1.0 M DTT, and 40 μL 1.0 M $MgCl_2$. The final reaction mixture was prepared by combining 1 part $^3$H-TTP, 4 parts $dH_2O$, 2.5 parts poly rA:oligo dT stock and 2.5 parts reaction buffer. Ten microliters of this reaction mixture was placed in a round bottom microtiter plate and 15 μL of virus containing supernatant was added and mixed. The plate was incubated at 37° C. for 60 min. Following incubation, the reaction volume was spotted onto DE81 filter-mats (Wallac), washed 5 times for 5 min each in a 5% sodium phosphate buffer or 2×SSC (Life Technologies). Next they were washed 2 times for 1 min each in distilled water, 2 times for 1 min each in 70% ethanol, and then dried. Incorporated radioactivity (counts per minute, CPM) was quantified using standard liquid scintillation techniques.

MTS Staining for Cell Viability

At assay termination, assay plates were stained with the soluble tetrazoliumbased dye MTS (3-(4,5-dimethylthiazol-2-yl)-5-(3-carboxymethoxyphenyl)-2-(4-sulfophenyl)-2H-tetrazolium; CellTiter 96 Reagent, Promega) to determine cell viability and quantify compound toxicity. The mitochondrial enzymes of metabolically active cells metabolize MTS to yield a soluble formazan product. This allows the rapid quantitative analysis of cell viability and compound cytotoxicity. The MTS is a stable solution that does not require preparation before use. At termination of the assay, 20 μL of MTS reagent was added per well. The microtiter plates were then incubated 4 h to 6 h at 37° C. The incubation intervals were chosen based on empirically determined times for optimal dye reduction. Adhesive plate sealers were used in place of the lids, the sealed plate was inverted several times to mix the soluble formazan product and the plate was read spectrophotometrically at 490/650 nm with a Molecular Devices SPECTRAMAXPLUS plate reader.

Determination of Virus Infectivity Using MAGI Cells

This assay uses MAGI cells (HeLa-CD4-LTR-β-gal cells; AIDS Research and Reference Reagent Repository, Bethesda, Md.), that contain one copy of the HIV-1 LTR promoter that drives expression of the β-galactosidase gene upon HIV-1 Tat transactivation. Thus, the expression of β-galactosidase was measured as a function of virus infection of the cells. Twenty-four hours prior to initiation of the assay, MAGI cells were plated in 96flatwell plates. On the day of the assay, media was removed from the wells and 50 μL of supernatant was transferred from the ACH-2 or H9/SK-1 cultures onto the MAGI cells. The plates were incubated for 1 h at 37° C. Fresh media (150 μL was then added to the wells for a final volume of 200'L. Plates were incubated for 7 d. A chemiluminescent endpoint was used to determine the extent of β-galactosidase expression as a measure of HIV-1 infection of the cells. At 7 d post infection, plates were aspirated and PBS was added to each well. Subsequently, detection of β-galactosidase activity was determined by measurement of relative chemiluminescence per manufacturer's instructions (TROPIX GAL-screen, Applied Biosystems, Bedford, Mass.).

Data Analysis

The $IC_{50}$ (50%, inhibition of virus replication) was calculated, $TC_{50}$ (50% reduction in cell viability), and a therapeutic index ($TI=IC_{50}/IC_{50}$) wre determined.

Compounds having useful activities against influenza as determined by this assay, viz. compounds having values of $IC_{50} \leq 30$ μmol include but are not limited to: 7-[bis(2-methoxyethyl)amino]-3H-phenothiazin-3-one, 7-(pyrrolidin-1-yl)-3H-phenothiazin-3-one, 1,9-dimethyl-7-(4-methylpiperazin-1-yl)-3H-phenothiazin-3-one, 7-[bis(2-methoxyethyl)amino]-1,9-dimethyl-3H-phenothiazin-3-one, 7-(dimethylamino)-3H-phenothiazin-3-one, 1,9-dimethyl-7-(morpholin-4-yl)-3H-phenothiazin-3-one, 1,9-dimethoxy-7-(pyrrolidin-1-yl)-3H-phenothiazin-3-one, 7-(dimethylamino)-1,9-dimethyl-3H-phenothiazin-3-one, 1,9-dichloro-7-(pyrrolidin-1-yl)-3H-phenothiazin-3-one, and 7-(azetidin-1-yl)-3H-phenothiazin-3-one.

REFERENCES

The following references are incorporated in there entireties and for all purposes.
1. Cloyd, M. W., and B. E. Moore. 1990. Spectrum of biological properties of human immunodeficiency virus (HIV-1) isolates. *Virology* 174:103-116.
2. C. Lackman-Smith, et al. 2008. Development of a Comprehensive Human Immunodeficiency Virus Type 1 Screening Algorithm for Discovery and Preclinical Testing of Topical Microbicides. *Antimicrobial Agents & Chemotherapy* 52(5):1768-1781.

HCV Live Virus Assay

HCV infection in cell culture was performed using Huh7 hepatoma cells transduced with a lentiviral vector containing a Gaussia luciferase reporter (G-Luc) gene as reported previously (see below); the luciferase reporter is secreted into the media and provides a convenient measure of cell number and viability. Measurement of virus replication (RNA replication, assembly, release, and infection) was enhanced by including a firefly luciferase reporter gene into the context of the Jc1 chimera. Since the firefly luciferase and the gaussia-luciferase utilize different substrates (luciferin, and coelenteracine, respectively) and were cell associated or secreted, respectively, both HCV replication and cell viability could be determined in parallel.

Jc1-F-Luc was transfected into Huh7-G-Luc cells and the test compound wasadded after four hours. Forty-eight hours post transfection (44 hours after compound addition), the media was removed and added to nave cells. Another 48 h later the inoculated cells were harvested and both firefly and gaussia luciferase activity was determined. In this assay format, the firefly luciferase activity was proportional to the efficiency of HCV replication in transfected cells, assembly of progeny particles in the transfected cells, the infectivity of the released particles and replication in the infected cells. Therefore, this type of assay interrogates the complete viral life cylcle, in principle allowing detection of interference with any phase of the viral replication process. Using cells transfected with subgenomic HCV replicons (lacking the structural proteins) we will specifically assess possible effects of selected compounds on HCV RNA replication and translation. Finally we will employ HCV pseudoparticles (HCVpp); i.e. retroviral or lentiviral cores surrounded by an envelope containing HCV glycoproteins to selectively analyze interference of any of the compounds with HCV entry. In addition to the HCV specific firefly luciferase signals we will assess gaussia luciferase activity to monitor cell number and viability. During the initial screening each individual compound will be analyzed in three different doses. Based on the HCV-specific dose response, compounds will be prioritized for more detailed characterization.

Compounds having useful activities against influenza as determined by this assay, viz. compounds having values of $IC_{50} \leq 30$ μmol include but are not limited to: 7-[bis(2-methoxyethyl)amino]-3H-phenothiazin-3-one, 7-(pyrrolidin-1-yl)-3H-phenothiazin-3-one, 7-(diethylamino)-3H-phenothiazin-3-one, 7-(pyrrolidin-1-yl)-3-oxo-3H-phenothiazine-9-carbonitrile, 1,9-dimethyl-7-(4-methylpiperazin-1-yl)-3H-phenothiazin-3-one, 7-[bis(2-methoxyethyl)amino]-1,9-dimethyl-3H-phenothiazin-3-one, 7-(dimethylamino)-1-

(trifluoromethyl)-3H-phenothiazin-3-one, 1,9-dimethyl-7-(morpholin-4-yl)-3H-phenothiazin-3-one, 1,9-dimethoxy-7-(4-methylpiperazin-1-yl)-3H-phenothiazin-3-one, 1,9-dimethoxy-7-(pyrrolidin-1-yl)-3H-phenothiazin-3-one, 7-[bis(2-methoxyethyl)amino]-3-oxo-3H-phenothiazine-1-carbonitrile, 7-(dimethylamino)-1,9-dimethyl-3H-phenothiazin-3-one, 1,9-dichloro-7-(pyrrolidin-1-yl)-3H-phenothiazin-3-one, and 1,9-dimethyl-7-[4-(propan-2-yl)piperazin-1-yl]-3H-phenothiazin-3-one, 7-(azetidin-1-yl)-3H-phenthiazin-3-one.

The following references are incorporated in there entireties and for all purposes.
1. Wakita, T. et al. "Production of infectious hepatitis C virus in tissue culture from a cloned viral genome." *Nat Med* 11, 791-6 (2005).
2. Zhong, J. et al. "Robust hepatitis C virus infection in vitro." *Proc Natl Acad Sci USA* 102, 9294-9 (2005).
3. Koutsoudakis, G. et al. "Characterization of the early steps of hepatitis C virus infection by using luciferase reporter viruses." *J Virol* 80, 5308-20 (2006).
4. Pietschmann, T. et al. "Construction and characterization of infectious intragenotypic and intergenotypic hepatitis C virus chimeras." *Proc Natl Acad Sci USA* 103, 7408-13 (2006).
5. de Chassey, B. et al. "Hepatitis C virus infection protein network." *Mol Syst Biol* 4, 230 (2008).
6. Bartosch, B., Dubuisson, J. & Cosset, F. "Infectious hepatitis C virus pseudoparticles containing functional E1-E2 envelope protein complexes." *J Exp Med* 197, 633-42 (2003).
7. Hsu, M. et al. "Hepatitis C virus glycoproteins mediate pH-dependent cell entry of pseudotyped retroviral particles." *Proc Natl Acad Sci USA* 100, 7271-6 (2003)

CONCLUSION

The above description of the embodiments, alternative embodiments, and specific examples, are given by way of illustration and should not be viewed as limiting. Further, many changes and modifications within the scope of the present embodiments may be made without departing from the spirit thereof, and the present invention includes such changes and modifications.

What is claimed:
1. A compound having the structure:

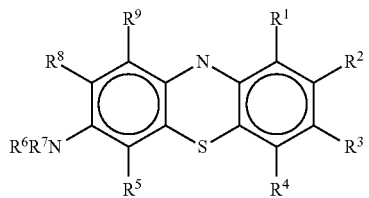

and its pharmaceutically acceptable salts and hydrates, wherein:
$R^9$ is selected from the group consisting of: halo, cyano, nitro, amino, carboxyl, formyl, sulfo, sulfinyl, sulfeno, sulfenamoyl, sulfonamino, and optionally substituted loweralkyl, loweralkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, loweralkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, loweralkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, diloweralkylamino, arylamino, diarylamino, aralkylamino, diaralkylamino, heteroarylamino, diheteroarylamino, heteroaralkylamino, diheteroaralkylamino, loweralkylsulfonyl, arylsulfonyl, heteroarylsulfonyl, cycloalkylsulfonyl, loweralkylsulfonyldioxy, arylsulfonyldioxy, heteroarylsulfonyldioxy, loweralkylsulfo, arylsulfo, heteroarylsulfo, cycloalkylsulfo, loweralkylsulfinyl, arylsulfinyl, heteroarylsulfinyl, cycloalkylsulfinyl, loweralkylsulfeno, arylsulfeno, heteroarylsulfeno, cycloalkylsulfeno, loweralkylsulfoamino, arylsulfoamino, heteroarylsulfoamino, cycloalkylsulfoamino, sulfonaloweralkylcarbonylsulfenamoyl, arylcarbonylsulfenamoyl, heteroarylcarbonylsulfenamoyl, cycloalkylcarbonylsulfenamoyl, cycloheteroalkylcarbonylsulfenamoyl, aralkylcarbonylsulfenamoyl, heteroaralkylcarbonylsulfenamoyl, (cycloalkyl)alkylcarbonylsulfenamoyl, (cycloheteroalkyl)alkylcarbonylsulfenamoyl, diloweralkylsulfenamoyl, arylsulfenamoyl, diarylsulfenamoyl, aralkylsulfenamoyl, diaralkylsulfenamoyl, heteroarylsulfenamoyl, diheteroarylsulfenamoyl, heteroaralkylsulfenamoyl, diheteroaralkylsulfenamoyl, loweralkylcarbonylsulfinamoyl, arylcarbonylsulfinamoyl, heteroarylcarbonylsulfinamoyl, cycloalkylcarbonylsulfinamoyl, cycloheteroalkylcarbonylsulfinamoyl, aralkylcarbonylsulfinamoyl, heteroaralkylcarbonylsulfinamoyl, (cycloalkyl)alkylcarbonylsulfinamoyl, (cycloheteroalkyl)alkylcarbonylsulfinamoyl, diloweralkylsulfinamoyl, arylsulfinamoyl, diarylsulfinamoyl, aralkylsulfinamoyl, diaralkylsulfinamoyl, heteroarylsulfinamoyl, diheteroarylsulfinamoyl, heteroaralkylsulfinamoyl, diheteroaralkylsulfinamoyl, loweralkyloxycarbonyl, aryloxycarbonyl, heteroaryloxycarbonyl, cycloalkyloxycarbonyl, cycloheteroalkyloxycarbonyl, aralyoxycarbonyloxycarbonyl, heteroaralkyloxycarbonyl, (cycloalkyl)alkyloxycarbonyl, (cycloheteroalkyl)alkyloxycarbonyl, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl;

$R^1$, $R^2$, $R^4$, $R^5$, and $R^8$ are selected independently from the group consisting of: hydrogen, halo, cyano, nitro, amino, carboxyl, formyl, sulfo, sulfinyl, sulfeno, sulfenamoyl, sulfonamino, and optionally substituted loweralkyl, loweralkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, loweralkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, loweralkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, diloweralkylamino, arylamino, diarylamino, aralkylamino, diaralkylamino, heteroarylamino, diheteroarylamino, heteroaralkylamino, diheteroaralkylamino, loweralkylsulfonyl, arylsulfonyl, heteroarylsulfonyl, cycloalkylsulfonyl, loweralkylsulfonyldioxy, arylsulfonyldioxy, heteroarylsulfonyldioxy, loweralkylsulfo, arylsulfo, heteroarylsulfo, cycloalkylsulfo, loweralkylsulfinyl, arylsulfinyl, heteroarylsulfinyl, cycloalkylsulfinyl, loweralkylsulfeno, arylsulfeno, heteroarylsulfeno, cycloalkylsulfeno, loweralkylsulfoamino, arylsulfoamino, heteroarylsulfoamino, cycloalkylsulfoamino, sulfonaloweralkylcarbonylsulfenamoyl, arylcarbonylsulfenamoyl, heteroarylcarbonylsulfenamoyl, cycloalkylcarbonylsulfenamoyl, cycloheteroalkylcarbonylsulfenamoyl, aralkylcarbonylsulfenamoyl, heteroaralkylcarbonylsulfenamoyl, (cycloalkyl)alkylcarbonylsulfenamoyl, (cycloheteroalkyl)alkylcarbonylsulfenamoyl, diloweralkylsulfenamoyl, arylsulfenamoyl, diarylsulfenamoyl, aralkylsulfenamoyl, diaralkylsulfenamoyl, heteroarylsulfenamoyl, diheteroarylsulfenamoyl, heteroaralkylsulfenamoyl, diheteroaralkylsulfenamoyl, loweralkylcarbonylsulfinamoyl, arylcarbonylsulfinamoyl, heteroarylcarbonylsulfinamoyl, cycloalkylcarbonylsulfinamoyl, cycloheteroalkylcarbonylsulfinamoyl, aralkylcarbonylsulfinamoyl, heteroaralkylcarbonylsulfinamoyl, (cycloalkyl)alkylcarbonylsulfinamoyl, (cycloheteroalkyl)alkylcarbonylsulfinamoyl, diloweralkylsulfinamoyl, arylsulfinamoyl, diarylsulfinamoyl, aralkylsulfinamoyl, diaralkylsulfinamoyl, heteroarylsulfenamoyl, diheteroarylsulfinamoyl, heteroaralkylsulfinamoyl, diheteroaralkylsulfinamoyl, loweralkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl;

$R^3$ is selected from the group consisting of: halo, oxo, imino, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl; and $R^6$ and $R^7$ are selected independently from the group consisting of: hydrogen and optionally substituted loweralkyl, loweralkyloxyloweralkyl, aminoloweralkyl, loweralkylaminoloweralkyl, diloweralkylaminoloweralkyl, aryl, aralkyl, heteroaryl, heteroaralkyl, arylcarbonyl, alkylcarbonyl, aralkylcarbonyl, heteroarylcarbonyl, and heteroaralkylcarbonyl; in addition, $R^6$ and $R^7$, together with the nitrogen atom to which each is attached, can form an optionally substituted 4-, 5-, 6-, or 7-membered ring wherein said optionally substituted is with a group which is hydrooxyl, nitro, amino, imino, cyano, halo, amidino, oxo, oxamidino, methoxamidino, imidino, guanidino, sulfonamido, carboxyl, formyl, lower alkyl, haloloweralkyl, loweralkoxy, haloloweralkoxy, lower alkoxyalkyl, alkylcarbonyl, arylcarbonyl, aralkylcarbonyl, heteroarylcarbonyl, heteroaralkylcarbonyl, aminoalkyl, or cyanoalkyl.

2. A compound of claim 1, wherein $R^3$ is oxo.

3. A compound of claim 2, wherein $R^6$ and $R^7$ forms an optionally substituted pyrrolidinyl ring with the nitrogen atom to which they are attached.

4. A compound of claim 3, wherein $R^6$ and $R^7$, together with the nitrogen atom to which they are attached, is optionally substituted pyrrolidin-1-yl.

5. A compound of claim 4, wherein at least one of $R^1$ and $R^9$ is selected from the group consisting of: halo, optionally substituted loweralkyloxy, and optionally substituted loweralkyl.

6. A compound of claim 5, wherein at least one of $R^1$ and $R^9$ is halo.

7. A compound of claim 6, wherein both $R^1$ and $R^9$ are halo.

8. A compound of claim 7, wherein $R^1$ and $R^9$ are selected from the group consisting of: chloro and fluoro.

9. A compound of claim 8, wherein $R^1$ and $R^9$ are both chloro or both fluoro.

10. A compound of claim 5, wherein at least one of $R^1$ and $R^9$ is loweralkyloxy.

11. A compound of claim 10, wherein both $R^1$ and $R^9$ are methoxy.

12. A compound of claim 2, wherein $R^6$ and $R^7$, together with the nitrogen atom to which they are attached, is optionally substituted piperazinyl.

13. A compound of claim 12, wherein $R^6$ and $R^7$, together with the nitrogen atom to which they are attached, is optionally substituted piperazin-1-yl.

14. A compound of claim 13, wherein both $R^1$ and $R^9$ are selected from the group consisting of halo and optionally substituted loweralkyl.

15. A compound of claim 14, wherein at least one of $R^1$ and $R^9$ is halo.

16. A compound of claim 15, wherein $R^1$ and $R^9$ are both chloro or both fluoro.

17. A compound of claim 14, wherein at least one of $R^1$ and $R^9$ is loweralkyl.

18. A compound of claim 17, wherein at least one of $R^1$ and $R^9$ is methyl.

19. A method for treating a viral disease in a mammal afflicted with such disease, wherein said viral disease is selected from the group consisting of HCV, HIV, influenza, Ebola virus, Marburg virus, Dengue virus, Venezuelean equine encephalitis, Chikungunya virus, and West Nile virus, Easter Equine Encephalitis, Western Equine Encephalitis, Monkey Pox, Corona Virus, Respiratory Syncytial Virus, Adenovirus, Human Rhinovirus, and Herpes Simplex Virus, comprising administering to such mammal a therapeutically effective amount of the compound having the structure:

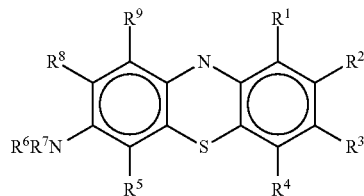

and its pharmaceutically acceptable salts and hydrates, wherein:

$R^1, R^2, R^4, R^5, R^8$, and $R^9$ are selected independently from the group consisting of: hydrogen, halo, cyano, nitro, amino, carboxyl, formyl, sulfo, sulfinyl, sulfeno, sulfenamoyl, sulfonamino, and optionally substituted loweralkyl, loweralkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, loweralkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, loweralkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, diloweralkylamino, arylamino, diarylamino, aralkylamino, diaralkylamino, heteroarylamino, diheteroarylamino, heteroaralkylamino, diheteroaralkylamino, loweralkylsulfonyl, arylsulfonyl, heteroarylsulfonyl, cycloalkylsulfonyl, loweralkylsulfonyldioxy, arylsulfonyldioxy, heteroarylsulfonyldioxy, loweralkylsulfo, arylsulfo, heteroarylsulfo, cycloalkylsulfo, loweralkylsulfinyl, arylsulfinyl, heteroarylsulfinyl, cycloalkylsulfinyl, loweralkylsulfeno, arylsulfeno, heteroaralkylsulfeno, cycloalkylsulfeno, loweralkylsulfoamino, arylsulfoamino, heteroarylsulfoamino, cycloalkylsulfoamino, sulfonaloweralkylcarbonylsulfenamoyl, arylcarbonylsulfenamoyl, heteroarylcarbonylsulfenamoyl, cycloalkylcarbonylsulfenamoyl, cycloheteroalkylcarbonylsulfenamoyl, aralkylcarbonylsulfenamoyl, heteroaralkylcarbonylsulfenamoyl, (cycloalkyl)alkylcarbonylsulfenamoyl, (cycloheteroalkyl)alkylcarbonylsulfenamoyl, diloweralkylsulfenamoyl, arylsulfenamoyl, diarylsulfenamoyl, aralkylsulfenamoyl, diaralkylsulfenamoyl, heteroarylsulfenamoyl, diheteroarylsulfenamoyl, heteroaralkylsulfenamoyl, diheteroaralkylsulfenamoyl, loweralkylcarbonylsulfinamoyl, arylcarbonylsulfinamoyl, heteroarylcarbonylsulfinamoyl, cycloalkylcarbonylsulfinarnoyl, cycloheteroalkylcarbonylsulfinamoyl, aralkylcarbonylsulfinamoyl, heteroaralkylcarbonylsulfinamoyl, (cycloalkyl)alkylcarbonylsulfinamoyl, (cycloheteroalkyl)alkylcarbonylsulfinamoyl, diloweralkylsulfinamoyl, arylsulfinamoyl, diarylsulfinamoyl, aralkylsulfinamoyl, diaralkylsulfenamoyl, heteroarylsulfinamoyl, diheteroarylsulfenamoyl, heteroaralkylsulfinamoyl, diheteroaralkylsulfenamoyl, loweralkyloxycarbonyl, aryloxycarbonyl, heteroaryloxycarbonyl, cycloalkyloxycarbonyl, cycloheteroalkyloxycarbonyl, aralyoxycarbonyloxycarbonyl, heteroaralkyloxycarbonyl, (cycloalkyl)alkyloxycarbonyl, (cycloheteroalkyl)alkyloxycarbonyl, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl;

$R^3$ is selected from the group consisting of: halo, oxo, imino, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl; and $R^6$ and $R^7$ are selected independently from the group consisting of: hydrogen and optionally substituted loweralkyl, loweralkyloxyloweralkyl, aminoloweralkyl, loweralkylaminoloweralkyl, diloweralkylaminoloweralkyl, aryl, aralkyl, heteroaryl, heteroaralkyl, arylcarbonyl, alkylcarbonyl, aralkylcarbonyl, heteroarylcarbonyl, and heteroaralkylcarbonyl; in addition, $R^6$ and $R^7$, together with the nitrogen atom to which each is attached, can form an optionally substituted 4-, 5-, 6-, or 7-membered ring wherein said optionally substituted is with a group which is hydrooxyl, nitro, amino, imino, cyano, halo, amidino, oxo, oxamidino, methoxamidino, imidino, guanidino, sulfonamido, carboxyl, formyl, lower alkyl, haloloweralkyl, loweralkoxy, haloloweralkoxy, lower alkoxyalkyl, alkylcarbonyl, arylcarbonyl, aralkylcarbonyl, heteroarylcarbonyl, heteroaralkylcarbonyl, aminoalkyl, or cyanoalkyl.

20. A compound of claim 2, wherein $R^6$ and $R^7$ are optionally substituted loweralkyl, alkyloxyalkyl, alkylaminoalkyl, and dialkylaminoalkyl.

21. A compound of claim 2, wherein $R^6$ and $R^7$ are optionally substituted lower alkyl or optionally substituted loweralkyloxyloweralkyl.

22. A compound of claim 2, wherein $R^6$ and $R^7$ are optionally substituted methyl, ethyl, or propyl.

23. A compound of claim 2, wherein $R^6$ and $R^7$ are optionally substituted methyl.

24. A compound of claim 1, wherein $R^6$ and $R^7$, together with the nitrogen atom to which each is attached, form an optionally substituted 4-, 5-, 6-, or 7-membered ring, and the ring is an optionally substituted pyrrolidinyl, piperidyl, morpholinyl, piperazinyl, azetidinyl, quinuclidinyl, or azepanyl.

25. A compound of claim 1, which is 7-(1,4-diazepan-1-yl)-1,9-dimethyl-phenothiazin-3-one.

26. A compound of claim 1, which is 7-(dimethylamino)-1,9-dimethyl-phenothiazin-3-one, 1,9-dimethyl-7-(4-methylpiperazin-1-yl)phenothiazin-3-one, 7-[bis(2-methoxyethyl)amino]-1,9-dimethylphenothiazin-3-one, 1,9-dimethyl-7-morpholino-phenothiazin-3-one, tert-butyl 4-(1,9-dimethyl-7-oxo-phenothizin-3-yl)piperazine-1-carboxylate, 1,9-dimethyl-7-piperazin-1-yl-phenothiazin-3-one, 1,9-dimethyl-7-pyrrolidin-1-yl-phenothiazin-3-one, tert-butyl 4-(1,9-dimethyl-7-oxo-phenothiazin-3-yl)-1,4-diazepane-1-carboxylate, 7-(azepan-1-yl)-1,9-dimethyl-phenothiazin-3-one, 7-(azetidin-1-yl)-1,9-dimethyl-phenothiazin-3-one, 7-(4-isopropylpiperazin-1-yl)-1,9-dimethylphenothiazin-3-one, 1,9-dimethyl-7-(4-methylsulfonylpiperazin-1-yl)phenothiazin-3-one, 1-(1,9-dimethyl-7-oxo-phenothiazin-3-yl)piperidine-4-carboxamide, 1,9-dimethyl-7-[4-(trifluoromethylsulfonyl)piperazin-1-yl]phenothiazin-3-one, 7-(4-isopropylsulfonylpiperazin-1-yl)-1,9-dimethyl-phenothiazin-3-one, 7-(4,4-difluoro-1-piperidyl)-1,9-dimethyl-phenothiazin-3-one, 1-(1,9-dimethyl-7-oxo-phenothiazin-3-yl)piperidine-4-carboxamidine, or 7-(azepan-1-yl)-1,9-diethyl-phenothiazin-3-one.

27. A compound of claim 1, which is 1,9-dichloro-7-pyrrolidin-1-yl-phenothiazin-3-one, 1,9-dichloro-7-(dimethylamino)phenothiazin-3-one, N-tert-butyl-4-(1,9-dichloro-7-oxo-phenothiazin-3-yl)piperazine-1-carboxamide, 7-[bis(2-methoxyethyl)amino]-1,9-dichlorophenothiazin-3-one, 4-(1,9-dichloro-7-oxo-phenothiazin-3-yl)-N,N-dimethyl-piperazine-1-sulfonamide, 1,9-dichloro-7-[4-(trifluoromethylsulfonyl)piperazin-1-yl]phenothiazin-3-one, tert-butyl 4-(1,9-dichloro-7-oxo-phenothiazin-3-yl)piperazine-1-carboxylate, or 1,9-difluoro-7-pyrrolidin-1-yl-phenothiazin-3-one.

28. A compound of claim 1, which is 1,9-dimethoxy-7-(4-methylpiperazin-1-yl)phenothiazin-3-one or 1,9-dimethoxy-7-pyrrolidin-1-yl-phenothiazin-3-one.

29. A compound of claim 1, which is 7-(dimethylamino)-1-fluoro-phenothiazin-3-one, 7-(dimethylamino)-1-(trifluoromethyl)phenothiazin-3-one, 7-[bis(2-methoxyethyl)

amino]-3-oxo-phenothiazine-1-carbonitrile, or 1-tert-butyl-7-pyrrolidin-1-yl-phenothiazin-3-one.

30. A method of claim 19, wherein said compound has the structure:

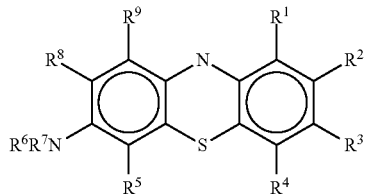

and its pharmaceutically acceptable salts and hydrates, wherein:

$R^9$ is selected from the group consisting of: halo, cyano, nitro, amino, carboxyl, formyl, sulfo, sulfinyl, sulfeno, sulfenamoyl, sulfonamino, and optionally substituted loweralkyl, loweralkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, loweralkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, loweralkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, diloweralkylamino, arylamino, diarylamino, aralkylamino, diaralkylamino, heteroarylamino, diheteroarylamino, heteroaralkylamino, diheteroaralkylamino, loweralkylsulfonyl, arylsulfonyl, heteroarylsulfonyl, cycloalkylsulfonyl, loweralkylsulfonyldioxy, arylsulfonyldioxy, heteroarylsulfonyldioxy, loweralkylsulfo, arylsulfo, heteroarylsulfo, cycloalkylsulfo, loweralkylsulfinyl, arylsulfinyl, heteroarylsulfinyl, cycloalkylsulfinyl, loweralkylsulfeno, arylsulfeno, heteroarylsulfeno, cycloalkylsulfeno, loweralkylsulfoamino, arylsulfoamino, heteroarylsulfoamino, cycloalkylsulfoamino, sulfonaloweralkylcarbonylsulfenamoyl, arylcarbonylsulfenamoyl, heteroarylcarbonylsulfenamoyl, cycloalkylcarbonylsulfenamoyl, cycloheteroalkylcarbonylsulfenamoyl, aralkylcarbonylsulfenamoyl, heteroaralkylcarbonylsulfenamoyl, (cycloalkyl)alkylcarbonylsulfenamoyl, (cycloheteroalkyl)alkylcarbonylsulfenamoyl, diloweralkylsulfenamoyl, arylsulfenamoyl, diarylsulfenamoyl, aralkylsulfenamoyl, diaralkylsulfenamoyl, heteroarylsulfenamoyl, diheteroarylsulfenamoyl, heteroaralkylsulfenamoyl, diheteroaralkylsulfenamoyl, loweralkylcarbonylsulfinamoyl, arylcarbonylsulfinamoyl, heteroarylcarbonylsulfinamoyl, cycloalkylcarbonylsulfinamoyl, cycloheteroalkylcarbonylsulfinamoyl, aralkylcarbonylsulfinamoyl, heteroaralkylcarbonylsulfinamoyl, (cycloalkyl)alkylcarbonylsulfinamoyl, (cycloheteroalkyl)alkylcarbonylsulfinamoyl, diloweralkylsulfinamoyl, arylsulfinamoyl, diarylsulfinamoyl, aralkylsulfinamoyl, diaralkylsulfinamoyl, heteroarylsulfinamoyl, diheteroarylsulfinamoyl, heteroaralkylsulfinamoyl, diheteroaralkylsulfinamoyl, loweralkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl;

$R^1$, $R^2$, $R^4$, $R^5$, and $R^8$ are selected independently from the group consisting of: hydrogen, halo, cyano, nitro, amino, carboxyl, formyl, sulfo, sulfinyl, sulfeno, sulfenamoyl, sulfonamino, and optionally substituted loweralkyl, loweralkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, loweralkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, loweralkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, diloweralkylamino, arylamino, diarylamino, aralkylamino, diaralkylamino, heteroarylamino, diheteroarylamino, heteroaralkylamino, diheteroaralkylamino, loweralkylsulfonyl, arylsulfonyl, heteroarylsulfonyl, cycloalkylsulfonyl, loweralkylsulfonyldioxy, arylsulfonyldioxy, heteroarylsulfonyldioxy, loweralkylsulfo, arylsulfo, heteroarylsulfo, cycloalkylsulfo, loweralkylsulfinyl, arylsulfinyl, heteroarylsulfinyl, cycloalkylsulfinyl, loweralkylsulfeno, arylsulfeno, heteroarylsulfeno, cycloalkylsulfeno, loweralkylsulfoamino, arylsulfoamino, heteroarylsulfoamino, cycloalkylsulfoamino, sulfonaloweralkylcarbonylsulfenamoyl, arylcarbonylsulfenamoyl, heteroarylcarbonylsulfenamoyl, cycloalkylcarbonylsulfenamoyl, cycloheteroalkylcarbonylsulfenamoyl, aralkylcarbonylsulfenamoyl, heteroaralkylcarbonylsulfenamoyl, (cycloalkyl)alkylcarbonylsulfenamoyl, (cycloheteroalkyl)alkylcarbonylsulfenamoyl, diloweralkylsulfenamoyl, arylsulfenamoyl, diarylsulfenamoyl, aralkylsulfenamoyl, diaralkylsulfenamoyl, heteroarylsulfenamoyl, diheteroarylsulfenamoyl, heteroaralkylsulfenamoyl, diheteroaralkylsulfenamoyl, loweralkylcarbonylsulfinamoyl, arylcarbonylsulfinamoyl, heteroarylcarbonylsulfinamoyl, cycloalkylcarbonylsulfinamoyl, cycloheteroalkylcarbonylsulfinamoyl, aralkylcarbonylsulfinamoyl, heteroaralkylcarbonylsulfinamoyl, (cycloalkyl)alkylcarbonylsulfinamoyl, (cycloheteroalkyl)alkylcarbonylsulfinamoyl, diloweralkylsulfinamoyl, arylsulfinamoyl, diarylsulfinamoyl, aralkylsulfinamoyl, diaralkylsulfinamoyl, heteroarylsulfinamoyl, diheteroarylsulfinamoyl, heteroaralkylsulfinamoyl, diheteroaralkylsulfinamoyl, loweralkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl;

$R^3$ is selected from the group consisting of: halo, oxo, imino, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl; and $R^6$ and $R^7$ are selected independently from the group consisting of: hydrogen and optionally substituted loweralkyl, loweralkyloxyloweralkyl, aminoloweralkyl, loweralkylaminoloweralkyl, diloweralkylaminoloweralkyl, aryl, aralkyl, heteroaryl, heteroaralkyl, arylcarbonyl, alkylcarbonyl, aralkylcarbonyl, heteroarylcarbonyl, and heteroaralkylcarbonyl; in addition, $R^6$ and $R^7$, together with the nitrogen atom to which each is attached, can form an optionally substituted 4-, 5-, 6-, or 7-membered ring wherein said optionally substituted is with a group which is hydrooxyl, nitro, amino, imino, cyano, halo, amidino, oxo, oxamidino, methoxamidino, imidino, guanidino, sulfonamido, carboxyl, formyl, lower alkyl, haloloweralkyl, loweralkoxy, haloloweralkoxy, lower alkoxyalkyl, alkylcarbonyl, arylcarbonyl, aralkylcarbonyl, heteroarylcarbonyl, heteroaralkylcarbonyl, aminoalkyl, or cyanoalkyl.

31. A method of claim 19, wherein said viral disease is selected from the group consisting of wherein said viral disease is selected from the group consisting of HCV, HIV, influenza, Ebola virus, Marburg virus, Dengue virus, Venezuelean equine encephalitis, Chikungunya virus, and West Nile virus.

32. A method of claim 19, wherein said viral disease is HIV.

33. A method of claim 19, wherein said viral disease is influenza.

34. A compound of claim 1, wherein said $R^6$ and $R^7$, together with the nitrogen atom to which each is attached, can form an optionally substituted cycloheteroalkyl ring.

35. A compound of claim 1, wherein said $R^6$ and $R^7$, together with the nitrogen atom to which each is attached, can form an optionally substituted cycloalkylamino ring.

36. A compound of claim 1, wherein said $R^6$ and $R^7$, together with the nitrogen atom to which each is attached, can form an optionally substituted cycloheteroalkylamino ring.

37. A compound of claim 1, wherein said $R^6$ and $R^7$, together with the nitrogen atom to which each is attached, can form an optionally substituted pyrrolidinyl, piperidyl, morpholinyl, piperazinyl, azetidinyl, quinuclidinyl, or azepanyl.

38. A method of claim 19, wherein said $R^6$ and $R^7$, together with the nitrogen atom to which each is attached, can form an optionally substituted cycloheteroalkyl ring.

39. A method of claim 19, wherein said $R^6$ and $R^7$, together with the nitrogen atom to which each is attached, can form an optionally substituted cycloalkylamino ring.

40. A method of claim 19, wherein said $R^6$ and $R^7$, together with the nitrogen atom to which each is attached, can form an optionally substituted cycloheteroalkylamino ring.

41. A method of claim 19, wherein said $R^6$ and $R^7$, together with the nitrogen atom to which each is attached, can form an optionally substituted pyrrolidinyl, piperidyl, morpholinyl, piperazinyl, azetidinyl, quinuclidinyl, or azepanyl.

* * * * *

UNITED STATES PATENT AND TRADEMARK OFFICE
CERTIFICATE OF CORRECTION

| | | |
|---|---|---|
| PATENT NO. | : 8,759,336 B2 | Page 1 of 1 |
| APPLICATION NO. | : 13/423141 | |
| DATED | : June 24, 2014 | |
| INVENTOR(S) | : Clarence R. Hurt et al. | |

It is certified that error appears in the above-identified patent and that said Letters Patent is hereby corrected as shown below:

ON THE TITLE PAGE OF THE PATENT

In Col. 1, please correct the spelling of the fifth inventor's last name as listed,

(75) Inventors:  Clarence R. Hurt, Los Altos, CA (US);

Vishwanath Lingappa, San Francisco, CA (US);

Beverly Freeman, Albany, CA (US);

Andy Atuegbu, Dublin, CA (US);

Anatoliy ~~Kitaygorodorskyy~~, San Francisco, CA (US)

to:

(75) Inventors:  Clarence R. Hurt, Los Altos, CA (US);

Vishwanath Lingappa, San Francisco, CA (US);

Beverly Freeman, Albany, CA (US);

Andy Atuegbu, Dublin, CA (US);

Anatoliy <u>Kitaygorodskyy</u>, San Francisco, CA (US)

Signed and Sealed this
Ninth Day of September, 2014

Michelle K. Lee
*Deputy Director of the United States Patent and Trademark Office*